United States Patent
Kobayashi et al.

(10) Patent No.: US 9,322,792 B2
(45) Date of Patent: Apr. 26, 2016

(54) X-RAY DIFFRACTION APPARATUS AND METHOD OF MEASURING X-RAY DIFFRACTION

(71) Applicant: RIGAKU CORPORATION, Akishima-shi, Tokyo (JP)

(72) Inventors: Shintaro Kobayashi, Akishima (JP); Toru Mitsunaga, Akishima (JP); Koichi Kajiyoshi, Akishima (JP); Kazuyoshi Arai, Akishima (JP)

(73) Assignee: RIGAKU CORPORATION, Tokyo (JP)

( * ) Notice: Subject to any disclaimer, the term of this patent is extended or adjusted under 35 U.S.C. 154(b) by 186 days.

(21) Appl. No.: 14/164,618

(22) Filed: Jan. 27, 2014

(65) Prior Publication Data
US 2015/0146861 A1    May 28, 2015

(30) Foreign Application Priority Data
Nov. 26, 2013 (JP) ................. 2013-243506

(51) Int. Cl.
*H05G 1/00* (2006.01)
*G01N 23/207* (2006.01)

(52) U.S. Cl.
CPC ...... *G01N 23/207* (2013.01); *G01N 2223/3301* (2013.01)

(58) Field of Classification Search
USPC ............................. 378/70, 71, 162, 163, 164
See application file for complete search history.

(56) References Cited

U.S. PATENT DOCUMENTS

| | | | |
|---|---|---|---|
| 6,295,076 B1* | 9/2001 | Gelbart | B41J 2/465 347/171 |
| 2010/0228501 A1* | 9/2010 | Cho | G03F 1/84 702/40 |
| 2013/0136333 A1* | 5/2013 | Dennerlein | G06K 9/00 382/132 |

FOREIGN PATENT DOCUMENTS

JP    A-2007-010486    1/2007

\* cited by examiner

*Primary Examiner* — Nicole Ippolito
(74) *Attorney, Agent, or Firm* — Oliff PLC

(57) ABSTRACT

There is provided an X-ray diffraction apparatus configured to irradiate a sample S on a sample stage with X-rays generated from an X-ray source and detect the X-rays diffracted by a sample using a detector, including a virtual mask setting section and a signal processing section. The detector outputs detection signals according to intensity of the X-rays received by detection elements, for each of the plurality of detection elements forming a detection surface. The virtual mask setting section is capable of setting a virtual mask on the detection surface of the detector, and setting at least an opening dimension of the virtual mask as an opening condition of the virtual mask independently in an X direction and a Y direction. The signal processing section processes the detection signals outputted from the detector according to the opening condition of the virtual mask set in the virtual mask setting section.

7 Claims, 20 Drawing Sheets

(A)

(B)

X-RAY DIFFRACTION APPARATUS AND METHOD OF MEASURING X-RAY DIFFRACTION

BACKGROUND

1. Field of the Invention

The present invention relates to an X-ray diffraction apparatus for irradiating a sample with X-rays and detecting the X-rays diffracted by the sample, and a method of measuring X-ray diffraction.

2. Description of the Related Art

As one of devices which analyze crystallinity and a crystal structure of a sample, an X-ray diffraction apparatus is known. The X-ray diffraction apparatus irradiates a sample with X-rays generated from an X-ray source, detects diffracted X-rays, and measures the intensity of the X-rays.

FIG. 27 is a schematic diagram illustrating a constitutional example of a measurement optical system of a conventional X-ray diffraction apparatus.

In FIG. 27, in a radiation direction of X-rays generated from an X-ray source 1, a paraboloidal multilayer mirror 2, a selection slit 3, an incidence soller slit 4, a length limiting slit 5, and an incidence slit 6 are disposed. An optical incidence system is constituted by these elements, for making X-rays be incident on a sample S set on a sample stage 7. The paraboloidal multilayer mirror 2 is installed in the optical incidence system as needed.

Meanwhile, in an emission direction of diffracted X-rays generated when the X-rays are made incident on the sample S of the sample stage 7, a front optical receiving slit 8, a Kβ filter 9, a parallel slit analyzer 10a, an optical receiving soller slit 10b, a rear optical receiving slit 11, an attenuator 12, and a detector 13 are disposed. An optical receiving system is constituted by these elements, for making the detector 13 receive the diffracted X-rays emitted from the sample S on the sample stage 7. The parallel slit analyzer 10a is installed in the optical receiving system as needed.

Relative positional relationship between the optical incidence system, the sample stage 7 and the optical receiving system is changeable by a goniometer not shown in the figure. The goniometer changes the relative positional relationship by rotating the optical incidence system and the optical receiving system by a prescribed angle each with an incident position of the X-rays made incident on a surface of the sample S set on the sample stage 7 as a rotation center.

The goniometer rotates the optical incidence system and the optical receiving system around a common rotation axis. In this case, when the optical incidence system is rotated in one direction, the optical receiving system is rotated reversely at the same angle. At the time, relative positions of the rotating directions of the optical incidence system and the optical receiving system are generally controlled such that relationship between an incidence angle of the X-rays made incident on the sample surface and a diffraction angle of the X-rays diffracted by the sample surface satisfies relationship of θ and 2θ.

In the X-ray diffraction apparatus including the measurement optical system composed of the above-described configuration, while synchronously rotating the optical incidence system and the optical receiving system by driving the goniometer, following measurement is performed in a predetermined scan angle range. Namely, the X-rays emitted from the X-ray source 1 to the sample stage 7 are fetched through the paraboloidal multilayer mirror 2 and the selection slit 3 to the incidence soller slit 4. The X-rays which have passed through the incidence soller slit 4 are radiated through the length limiting slit 5 and the incidence slit 6 to the surface of the sample S on the sample stage 7.

Meanwhile, the diffracted X-rays emitted from the surface of the sample S by the irradiation of the X-rays are fetched through the front optical receiving slit 8 and the Kβ filter 9 to the parallel slit analyzer 10a and the optical receiving soller slit 10b. The diffracted X-rays which have passed through the optical receiving soller slit 10b pass through the rear optical receiving slit 11 and the attenuator 12 and reach the detector 13, and the intensity of incident X-rays is detected.

In the conventional X-ray diffraction apparatus, when limiting a dose of the X-rays incident on the detector 13 in the rear optical receiving slit 11, a resolution of measurement (hereinafter, called "measurement resolution") varies depending on how much slit width is used for limiting the dose. Namely, when the slit width of the rear optical receiving slit 11 is relatively narrow as illustrated in FIG. 28(A), since a fetch angle of the X-rays in the view from the center of the goniometer becomes narrow, the measurement resolution when detecting the X-rays using the detector 13 becomes relatively high. Meanwhile, when the slit width of the rear optical receiving slit 11 is relatively wide as illustrated in FIG. 28(B), since the fetch angle of the X-rays in the view from the center of the goniometer becomes wide, the measurement resolution when detecting the X-rays using the detector 13 becomes relatively low.

Accordingly, when the measurement resolution is desired to be changed, the slit width of the rear optical receiving slit 11 needs to be changed. There are mainly two methods of changing the slit width of the rear optical receiving slit 11. One is a method in which the rear optical receiving slit 11 is configured to be attachable and detachable by a manual insertion method and the slit width is changed by exchanging the slit by manual insertion. The other one is a method in which the rear optical receiving slit 11 includes an opening/closing mechanism for opening and closing the rear optical receiving slit 11 and the slit width of the rear optical receiving slit 11 is changed by the opening/closing mechanism (for instance, see Patent Document 1, Japanese Patent Laid-Open No. 2007-10486).

Conventionally, a user who uses the X-ray diffraction apparatus sets the slit width of the rear optical receiving slit 11 by the slit exchange or the opening/closing mechanism, and by operating the X-ray diffraction apparatus under the set condition, X-ray diffraction is measured by a desired measurement resolution. Also, conventionally, an X-ray diffraction apparatus is known which adopts a strip type sensor configuration in which thin and long sensors are arranged adjacently to each other as a configuration of a detector provided in the X-ray diffraction apparatus and allows a user to select which of the adjacent sensors is to be used to perform measurement.

The detector used in the X-ray diffraction apparatus is divided into, for instance, a zero-dimensional detector and a one-dimensional detector depending on whether or not the resolution of a position (hereinafter, called "position resolution") is provided on the detection surface. The zero-dimensional detector is the detector not having the position resolution on the detection surface, and the one-dimensional detector is the detector having the position resolution in one direction on the detection surface. In the X-ray diffraction apparatus using the detectors, by changing the slit width of the rear optical receiving slit 11 as described above, the measurement resolution can be changed.

In a type of exchanging the slit by the manual insertion method, it is necessary to exchange the slit in order to change the measurement resolution. However, the slit is frequently exchanged so as to be suited to a desired measurement condition when adjusting an optical system or a sample position or when actually performing measurement. Therefore, there is a problem that it takes time and labor to change the measurement resolution by slit exchange.

Meanwhile, in a type including the opening/closing mechanism of the slit, since the slit width can be changed by the opening/closing operation of the slit, the time and labor accompanying the slit exchange can be saved. However, since the opening/closing mechanism of the slit is expensive compared to the type of exchanging the slit by the manual insertion method, there is a problem that it causes cost increase of the X-ray diffraction apparatus. Also, when disposing a monochromator crystal or an analyzer crystal in an optical path of the X-rays from the sample S on the sample stage 7 to the detector 13 to detect the X-rays by a higher measurement resolution, the cost is increased further. The reason is as follows.

Namely, in the measurement optical system illustrated in FIG. 29(A), the X-rays are incident on the detector 13 through the rear optical receiving slit 11 and the attenuator 12. In this case, in order to increase the measurement resolution without changing the slit width of the rear optical receiving slit 11, it is effective to remove an unneeded element by installing two monochromator crystals 14a and 14b at a front portion before the rear optical receiving slit 11 and reflecting the X-rays by the respective monochromator crystals 14a and 14b as illustrated in FIG. 29(B). However, in that case, before and after installing the monochromator crystals 14a and 14b, a position of the X-rays incident on the detection surface of the detector 13 is shifted by L. Therefore, in the type including the opening/closing mechanism of the slit, a moving mechanism is separately required for shifting an opening/closing center position of the rear optical receiving slit 11 by mechanically moving a slit position of the rear optical receiving slit 11 according to a shift amount L of the incident position of the X-rays, thus resulting in a further cost increase.

The main object of the present invention is to provide an X-ray diffraction apparatus and an X-ray diffraction method capable of changing the measurement resolution without using the rear optical receiving slit and flexibly coping with the change of the measurement resolution that cannot be realized when using the rear optical receiving slit.

SUMMARY OF THE INVENTION

The present inventors have examined various possibilities in the case of using a two-dimensional detector as a detector for detecting X-rays from a sample, regardless of the object of obtaining an intensity distribution or the like of the X-rays in a wide range, which is the main object of using the two-dimensional detector. As a result, it is found that a physical operation of "changing the measurement resolution" performed conventionally by the replacement or opening/closing mechanism of a rear optical receiving slit, can be realized without the rear optical receiving slit. Further, based on the above concept, a novel concept capable of realizing an unconventional new method of measuring X-ray diffraction is obtained. Thus, the present invention is achieved.

A first aspect of the present invention is, an X-ray diffraction apparatus which irradiates a sample set on a sample stage with X-rays generated from an X-ray source, and detects the X-rays diffracted by the sample using a detector which has a detection surface formed of a plurality of detection elements arrayed two-dimensionally in a first direction and a second direction that are perpendicular to each other, and outputs a detection signal according to intensity of the X-rays received by the detection element, for each of the plurality of detection elements forming the detection surface, the X-ray diffraction apparatus comprising:

a virtual mask setting section capable of setting a virtual mask on the detection surface of the detector and setting at least an opening dimension of the virtual mask as an opening condition of the virtual mask independently in the first direction and the second direction; and a signal processing section which processes the detection signal outputted from the detector according to the opening condition of the virtual mask set in the virtual mask setting section.

A second aspect of the present invention is, the X-ray diffraction apparatus according to the first aspect, wherein the virtual mask setting section is capable of setting an opening center position of the virtual mask in addition to the opening dimension of the virtual mask, as the opening condition of the virtual mask.

A third aspect of the present invention is, the X-ray diffraction apparatus according to the first or second aspect, wherein the virtual mask setting section is capable of setting the number of openings of the virtual mask in addition to the opening dimension of the virtual mask, as the opening condition of the virtual mask.

A fourth aspect of the present invention is, the X-ray diffraction apparatus according to any one of the first-third aspects, wherein the virtual mask setting section is capable of setting an opening shape of the virtual mask in addition to the opening dimension of the virtual mask, as the opening condition of the virtual mask.

A fifth aspect of the present invention is, the X-ray diffraction apparatus according to any one of the first-fourth aspects, wherein the virtual mask setting section is capable of setting an inclination angle of an opening of the virtual mask in addition to the opening dimension of the virtual mask, as the opening condition of the virtual mask.

A sixth aspect of the present invention is, the X-ray diffraction apparatus according to any one of the first-fifth aspects, comprising a dimensional mode setting section which sets a dimensional mode applied when measuring X-ray diffraction using the detector, wherein the signal processing section processes the detection signal outputted from the detector according to the dimensional mode set in the dimensional mode setting section.

A seventh aspect of the present invention is, a method of measuring X-ray diffraction which irradiates a sample set on a sample stage with X-rays generated from an X-ray source, and detects the X-rays diffracted by the sample using a detector which has a detection surface formed of a plurality of detection elements arrayed two-dimensionally in a first direction and a second direction that are perpendicular to each other, and outputs a detection signal according to intensity of the X-rays received by the detection element, for each of the plurality of detection elements forming the detection surface, the method comprising:

a virtual mask setting step of setting a virtual mask on the detection surface of the detector and setting at least an opening dimension of the virtual mask as an opening condition of the virtual mask independently in the first direction and the second direction;

an X-ray detecting step of irradiating the sample set on the sample stage with the X-rays generated from the X-ray source, and detecting the X-rays diffracted by the sample using the detector; and a signal processing step of processing the detection signal outputted from the detector in the X-ray detecting step, according to the opening condition of the virtual mask set in the virtual mask setting step.

According to the present invention, a measurement resolution can be changed without using a rear optical receiving slit and the change of the measurement resolution that cannot be realized when using the rear optical receiving slit can be flexibly coped with.

DETAILED DESCRIPTION OF THE EMBODIMENT

Figure 1:
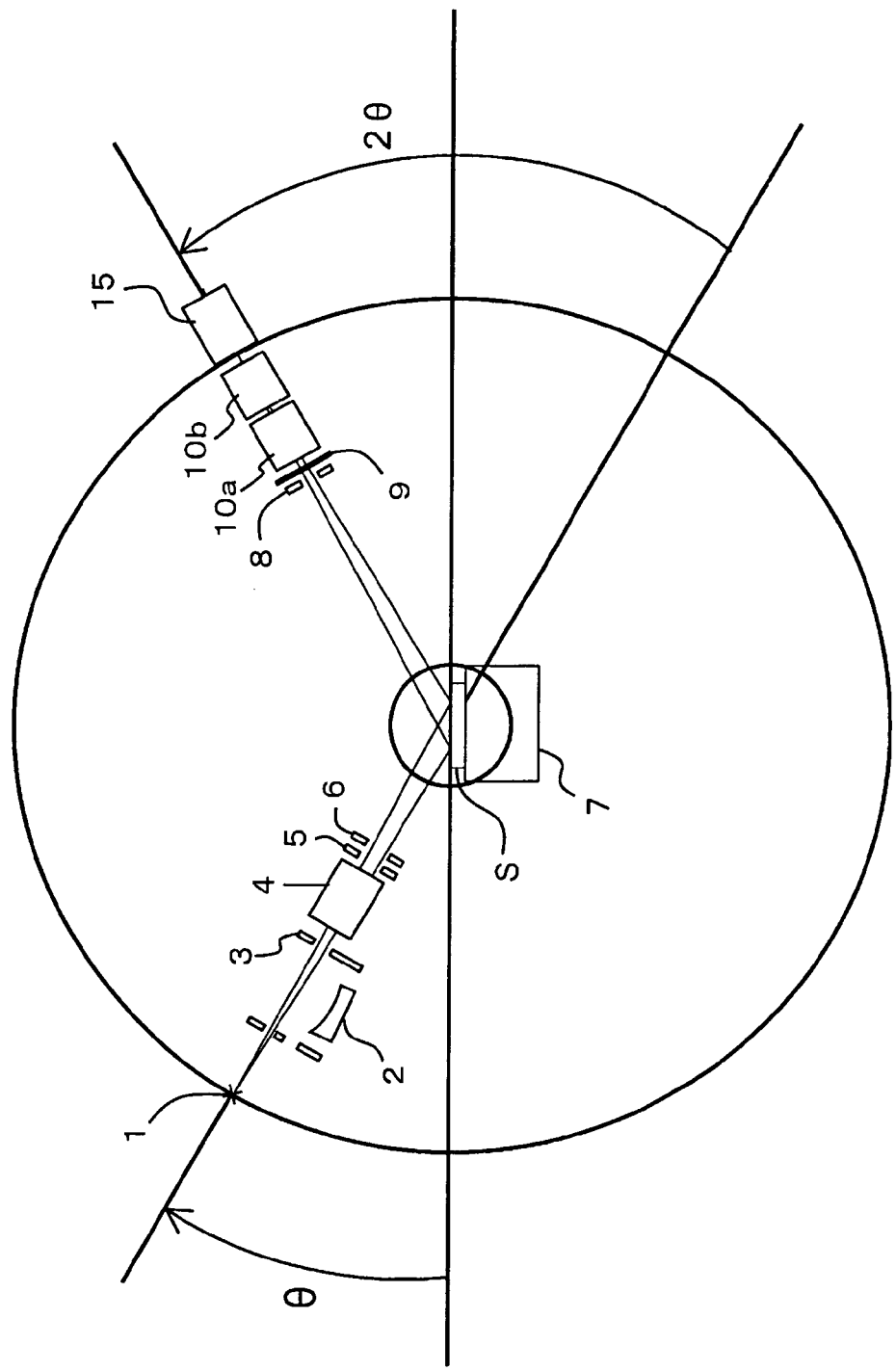
FIG. 1 is a schematic diagram illustrating a constitutional example of a measurement optical system of an X-ray diffraction apparatus according to an embodiment of the present invention.

Hereinafter, an embodiment of the present invention will be described in detail with reference to the drawings.

In the embodiment of the present invention, descriptions will be given in the following order.

1. Measurement optical system of X-ray diffraction apparatus
2. First constitutional example of X-ray diffraction apparatus
3. Method of measuring X-ray diffraction
4. First example of setting screen of virtual mask
5. Relationship between opening condition of virtual mask and signal processing
6. Second example of setting screen of virtual mask
7. Second constitutional example of X-ray diffraction apparatus
8. Effects of embodiment
9. Modifications or the like 1. Measurement Optical System of X-Ray Diffraction Apparatus FIG. 1 is a schematic diagram illustrating a constitutional example of a measurement optical system of an X-ray diffraction apparatus according to an embodiment of the present invention.

In FIG. 1, in a radiation direction of X-rays generated from an X-ray source 1, a paraboloidal multilayer mirror 2, a selection slit 3, an incidence soller slit 4, a length limiting slit 5, and an incidence slit 6 are disposed. An optical incidence system is constituted by these elements, for making X-rays be incident on a sample S set on a sample stage 7. The paraboloidal multilayer mirror 2 is installed in the optical incidence system as needed.

The X-ray source 1 generates the X-rays to be made incident on the sample S. The paraboloidal multilayer mirror 2 makes the X-rays radiated from the X-ray source 1 be parallel and monochromatic. The selection slit 3 intercepts passing of an element unneeded for the measurement of the X-ray diffraction. The selection slit 3 is disposed on an emission side of the paraboloidal multilayer mirror 2. The incidence soller slit 4 suppresses vertical divergence of the X-rays made incident through the selection slit 3. The length limiting slit 5 limits a width through which the X-rays pass in a longitudinal direction of a cross section of the X-rays that have passed through the incidence soller slit 4. The incidence slit 6 limits a divergence angle of the X-rays in a short direction of the cross section of the X-rays. The sample stage 7 holds the sample S to be a measurement object of the X-ray diffraction.

Meanwhile, in an emission direction of the X-rays which are made incident on the sample S set on the sample stage 7 and diffracted by the sample S, a front optical receiving slit 8, a Kβ filter 9, a parallel slit analyzer 10a, an optical receiving soller slit 10b, and a detector 15 are disposed. An optical receiving system is constituted by these elements, for making the detector 15 receive the diffracted X-rays emitted from the sample S on the sample stage 7. The parallel slit analyzer 10a is installed in the optical receiving system as needed. Also, in the optical receiving system, a rear optical receiving slit for changing the measurement resolution and an attenuator for attenuating the X-rays are not provided. The reason will be described later.

The front optical receiving slit 8 intercepts scattered rays of the diffracted X-rays from the sample S. The Kβ filter 9 eliminates Kβ rays. The parallel slit analyzer 10a makes the X-rays that are nearly parallel pass through. The optical receiving soller slit 10b suppresses the horizontal divergence of the X-rays made incident through the front optical receiving slit 8 and the Kβ filter 9. The horizontal divergence is the divergence of the X-rays in a direction orthogonal to a scan direction (2θ direction) of the detector 15 when the X-rays generated from the X-ray source 1 advance while being diverged conically around the X-ray source 1.

Figure 2:
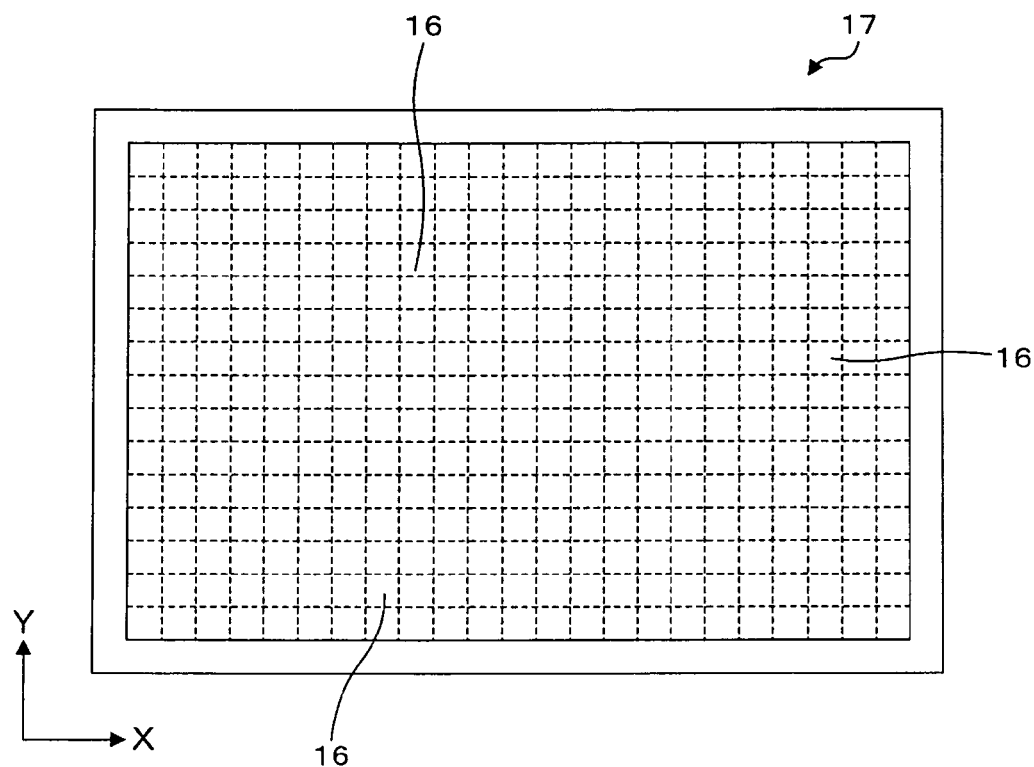
FIG. 2 is a schematic view when viewing a detection surface of a detector from the front.

The detector 15 is, as illustrated in FIG. 2, a two-dimensional detector forming one rectangular detection surface 17 by a plurality of two-dimensionally arrayed detection elements 16. The respective detection elements 16 are arranged in a grid shape in a first direction ("X direction", hereinafter) and a second direction ("Y direction", hereinafter) that are perpendicular to each other. As for the size of the detection surface 17, a rectangle is about 85 mm in the dimension (total width) of the X direction and about 35 mm in the dimension (total height) of the Y direction, and the size of the respective detection elements 16 is a 100 μm square for instance. In the following descriptions, as a matter of convenience, the X direction is expressed as a horizontal direction, and the Y direction is expressed as a vertical direction.

The respective detection elements 16 detect the intensity of the X-rays made incident thereon respectively. Specifically, when the X-ray is made incident on a certain detection element 16, the detection element 16 generates a detection signal (electric signal or the like) proportional to the intensity of the incident X-ray. Therefore, when detecting the X-rays using the detector 15, the detection signals for the number of the detection elements 16 forming the detection surface 17 are obtained.

Also, the detector 15 has a two-dimensional position resolution. The position resolution is a function of identifying an incident position of the X-rays made incident on the detection surface 17. Also, a one-dimensional position resolution is the position resolution realized by one-dimensionally arraying the detection elements, and the two-dimensional position resolution is the position resolution realized by two-dimensionally arraying the detection elements.

On the detection surface 17 of the detector 15, to each of the respective detection elements 16, position information capable of specifying (identifying) the position of the detection element 16 is allocated. To be described specifically, for instance, an intrinsic column number is allocated to each column of the detection elements 16 in the X direction, and an intrinsic row number is allocated to each row of the detection elements 16 in the Y direction. Then, by combining the row number and the column number, the position of the detection elements 16 can be uniquely specified.

The detector 15 outputs the detection signal for each of the respective detection elements 16 in association with the position information. Therefore, as for the detection signal outputted from the detector 15, it is possible to discriminate by the detection element 16 present at what position within the detection surface 17 the detection signal is generated. Thus, the electric signals outputted from the plurality of detection elements 16 indicate a two-dimensional intensity distribution of the X-rays made incident on the detection surface 17.

Relative positional relationship between the optical incidence system, the sample stage 7 and the optical receiving system is changeable by a goniometer not shown in the figure. The goniometer changes the relative positional relationship of the optical incidence system and the optical receiving system in a rotating direction around a rotation axis not shown in the figure. Specifically, relative positions of the optical incidence system, the sample stage 7 and the optical receiving system are changed so that the position of the detector 15 is changed on a circumference (also called "gonio-circle", hereinafter) around the rotation axis when an incidence angle of the X-rays made incident on the surface of the sample S on the sample stage 7 is changed.

Regarding the goniometer, there are mainly two types. One is a type of rotating the sample stage 7 to the optical incidence system and rotating the optical receiving system in synchronism with it. The other is a type of synchronously rotating the optical incidence system and the optical receiving system while keeping the sample stage 7 fixed in a horizontal state. In this embodiment, as one example, the goniometer of the latter type is adopted.

In this case, generally, the goniometer rotates the optical incidence system and the optical receiving system around the rotation axis while keeping the sample S in a planar shape that is horizontally placed on the sample stage 7 fixed when measuring the X-ray diffraction. When the optical incidence system is rotated in one direction, the optical receiving system is rotated at the same angle in a direction opposite to it. At the time, relative positions of the rotating directions of the optical incidence system and the optical receiving system are controlled such that relationship between the incidence angle of the X-rays made incident on the surface of the sample S and a diffraction angle of the X-rays diffracted by the surface of the sample S satisfies relationship of θ and 2θ illustrated in FIG. 1.

2. First Constitutional Example of X-Ray Diffraction Apparatus

Figure 3:
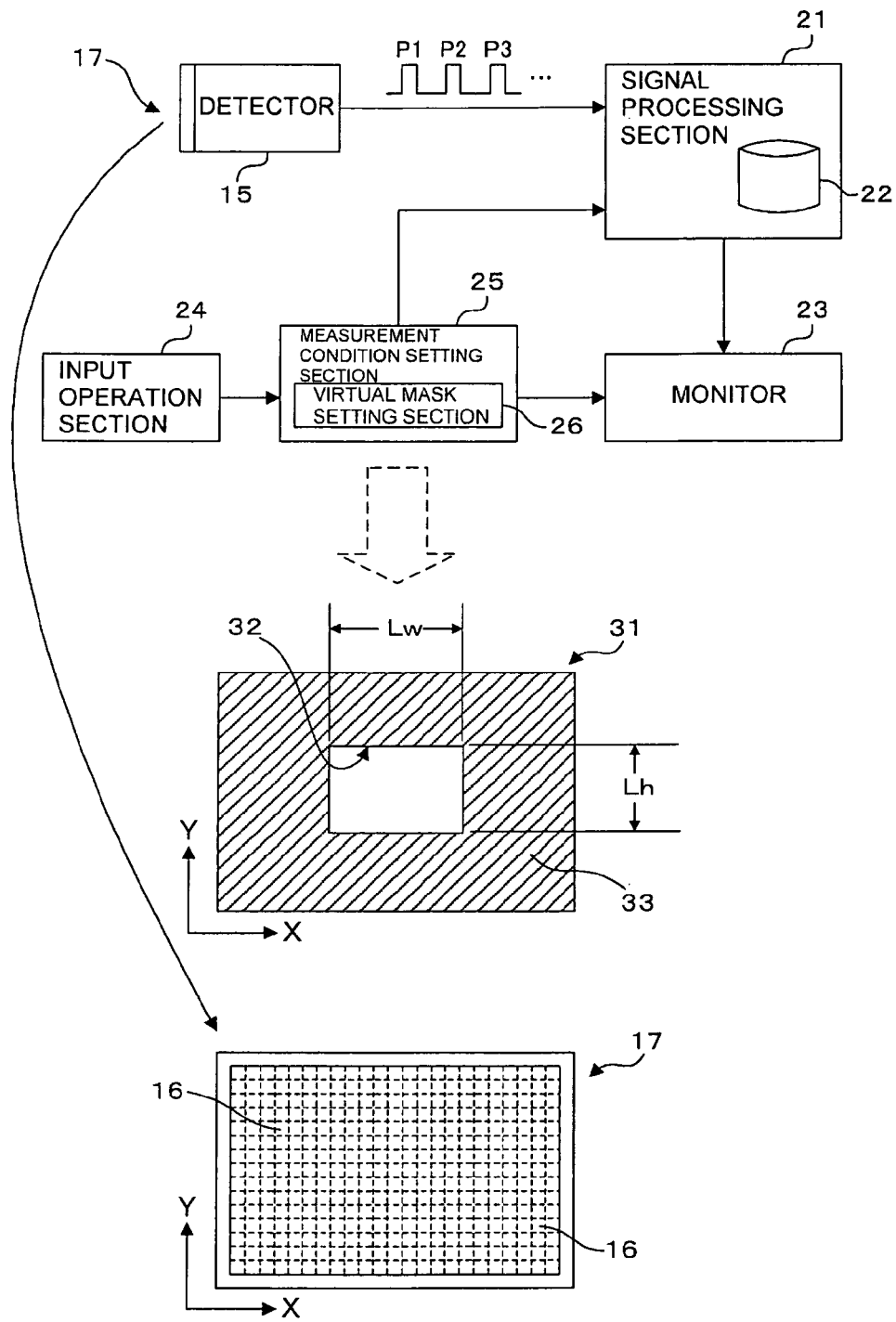
FIG. 3 is a functional block diagram illustrating a first constitutional example of the X-ray diffraction apparatus according to an embodiment of the present invention.

FIG. 3 is a functional block diagram illustrating a first constitutional example of the X-ray diffraction apparatus according to an embodiment of the present invention. In FIG. 3, the detection signals outputted from the detector 15 are fetched to a signal processing section 21.

The signal processing section 21 executes various kinds of signal processing to the detection signals obtained by the detector 15. The signal processing section 21 comprises, for instance, a digital signal processor (DSP) which is a microprocessor specialized in digital signal processing, a microcomputer, or a signal processing circuit of a hardware configuration or the like. The signal processing section 21 has at least one (generally called "memory 22", hereinafter) of an internal memory and an external memory, and data can be stored in the memory 22 as needed. As a program for the signal processing, there are various programs according to the object of measurement by the X-ray diffraction, such as an analysis program, an operation program, a program for operation control, and a drawing program for display and printing. These programs are incorporated in the signal processing section 21 beforehand.

A result of processing such as analysis, etc., applied in the by the signal processing section 21 is displayed on a monitor 23 as the result of measuring the sample by the X-ray diffraction. The monitor 23 is used for displaying the measurement result, displaying a setting screen for setting a measurement condition using a measurement condition setting section 25 or displaying other screens. The monitor 23 is configured using a liquid crystal display or an organic EL display or the like, for instance.

An input operation section 24 is operated by a user using the X-ray diffraction apparatus in order to input information needed when using the X-ray diffraction apparatus. The input operation section 24 is configured using an input device such as a mouse or a keyboard or a touch panel attached to the monitor 23 or the like, for instance.

The measurement condition setting section 25 is provided for setting a condition of measurement by the X-ray diffraction by the user of the X-ray diffraction apparatus. When the user sets the condition of the measurement by the X-ray diffraction, the measurement condition setting section 25 makes the monitor 23 display the setting screen for that, and receives the measurement condition specified by the user through the input operation section 24. There are various measurement conditions that can be set in the measurement condition setting section 25 such as a scan condition (a scan start angle, a scan end angle, a scan step width) when rotationally moving the detector 15 by the drive of the goniometer, for instance, and a virtual mask setting section 26 is provided as one of the setting function sections.

The virtual mask setting section 26 sets a virtual mask 31 on the detection surface 17 of the detector 15. The "virtual mask" described in this specification is a mask which does not physically exist and is a mask virtually set on the detection surface 17 of the detector 15. The virtual mask 31 includes an opening part 32 and a shield part 33. The opening part 32 does not cover the respective detection elements 16 of the detection surface 17 when the virtual mask 31 is set on the detection surface 17, and the shield part 33 covers the respective detection elements 16 of the detection surface 17. However, since the virtual mask 31 is not a physical mask, even when the virtual mask 31 is set on the detection surface 17, incidence of the X-rays on the detection surface 17 is not limited by the setting of the virtual mask 31.

In the virtual mask setting section 26, as an opening condition of the virtual mask, at least an opening dimension of the virtual mask 31 can be set independently in the X direction and the Y direction. The opening dimension of the virtual mask 31 is defined by a dimension Lw in the X direction, and is defined by a dimension Lh in the Y direction. The opening condition of the virtual mask set in the virtual mask setting section 26 is notified from the virtual mask setting section 26 to the signal processing section 21. Then, when measuring the actual X-ray diffraction, in the case that the virtual mask is set on the detection surface 17 of the detector 15 by the virtual mask setting section 26, the detection signals outputted from the detector 15 are signal-processed by the signal processing section 21 according to the opening condition of the virtual mask. Relationship between the opening condition of the virtual mask and the signal processing will be described later.

3. Method of Measuring X-Ray Diffraction

Next, a method of measuring X-ray diffraction which can be realized using the X-ray diffraction apparatus according to an embodiment of the present invention will be described. The Method of measuring X-ray diffraction includes a virtual mask setting step using the virtual mask setting section 26, an X-ray detecting step by the measurement optical system, and a signal processing step by the signal processing section 21.

First, a basic operation of the X-ray diffraction apparatus composed of the above-described configuration will be described.

When performing X-ray diffraction measurement using the X-ray diffraction apparatus, prior to the measurement, the optical system is adjusted and a position of the sample S set on the sample stage 7 is adjusted or the like. Then, a user specifies the measurement condition of the X-ray diffraction (including the opening condition of the virtual mask) using the measurement condition setting section 25, and then an operation of instructing start of the measurement is performed. Thus, the X-ray diffraction apparatus performs the X-ray diffraction measurement of the sample according to the measurement condition specified by the user. Specifically, the X-ray diffraction apparatus is operated as follows.

First, by driving the goniometer, the optical incidence system and the optical receiving system start rotation around the common rotation axis (not shown in the figure) respectively from a predetermined scan start position. Thereafter, at the point of time at which the optical incidence system and the optical receiving system are rotated to a predetermined scan end position, the goniometer is stopped. During the rotation, in the optical incidence system, the X-rays generated from the X-ray source 1 are made incident on the surface of the sample S on the sample stage 7 through the paraboloidal multilayer mirror 2, the selection slit 3, the incidence soller slit 4 and the length limiting slit 5.

Meanwhile, in the optical receiving system, the X-rays diffracted by the surface of the sample S are made incident on the detection surface 17 of the detector 15 through the front optical receiving slit 8, the Kβ filter 9, the parallel slit analyzer 10a and the optical receiving soller slit 10b. At the time, the detector 15 is moved in the rotating direction (2θ direction in the figure) while disposing the detection surface 17 on the gonio-circle. The direction in which the detector 15 is rotationally moved is a direction along the Y direction of the detection surface 17. Also, while the detector 15 is rotationally moved, the detection signals according to the intensity of the X-rays are outputted from the respective detection elements 16 of the detection surface 17.

The detection signals outputted by the respective detection elements 16 of the detector 15 are read to the signal processing section 21 in respective rising period every time read pulses P1, P2, P3, . . . that rise in a fixed cycle rise. Also, to the signal processing section 21, information of a scan angle of the detector 15 rotationally moved by the drive of the goniometer is fetched. Then, in the signal processing section 21, the detection signals read from the respective detection elements 16 and the information of the scan angle of the detector 15 are stored in the memory 22 in association with each other. Thus, as the measurement result of the X-ray diffraction of the sample S, for instance, a graph taking the X-ray intensity for a vertical axis and a diffraction angle for a horizontal axis is displayed on the monitor 23.

Next, the opening condition of the virtual mask set using the virtual mask setting section 26 and a concrete example of the signal processing of the signal processing section 21 based on the opening condition of the virtual mask will be described.

4. First Example of Setting Screen of Virtual Mask

Figure 4:
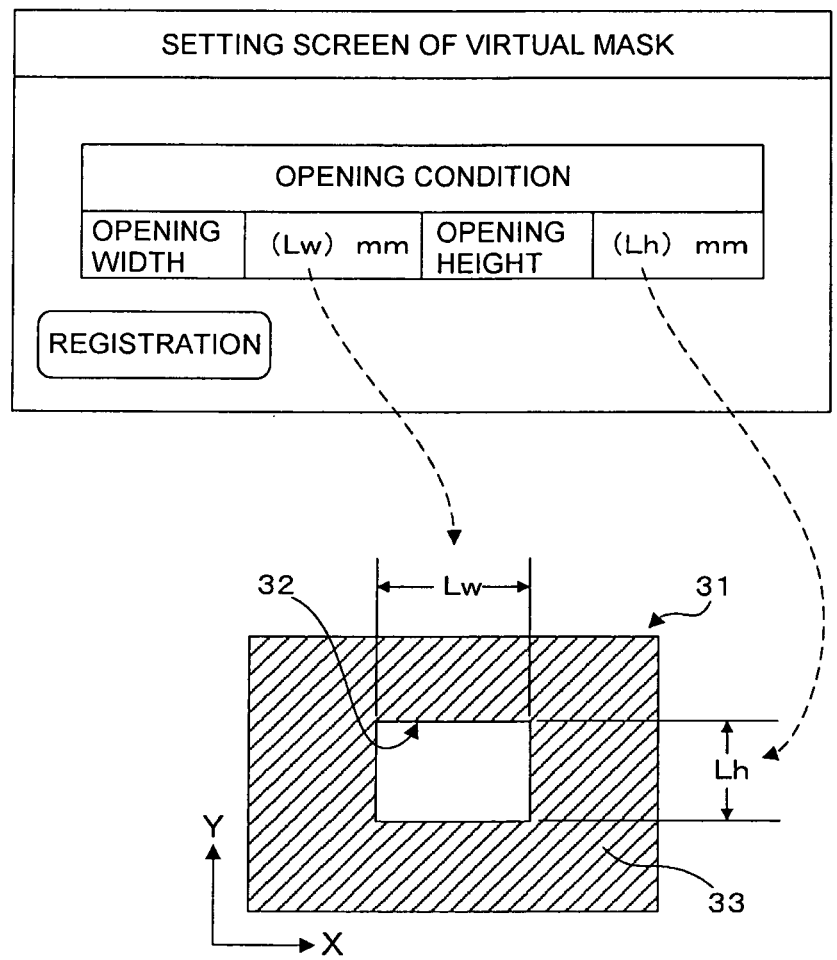
FIG. 4 is a diagram illustrating a first example of a setting screen of a virtual mask displayed on a monitor by a virtual mask setting section.

FIG. 4 is a diagram illustrating a first example of a setting screen of the virtual mask displayed on the monitor by the virtual mask setting section. In FIG. 4, while an image picture of the virtual mask 31 is displayed below "the setting screen of the virtual mask", the image picture may be displayed as needed. This point is similar in the following descriptions. On the setting screen of the virtual mask shown in the figure, the opening dimension to be one of the opening conditions of the virtual mask can be specified by the opening width Lw of the virtual mask and the opening height Lh of the virtual mask. On the setting screen of the virtual mask, the opening width Lw and the opening height Lh can be specified in millimeters, respectively.

The virtual mask setting section 26 has a function of calculating how many detection elements 16 the opening dimension set in millimeters by the user on the setting screen of the virtual mask corresponds to, or a conversion table for that. Then, when the user specifies the opening dimension of the virtual mask in millimeters, by converting the specified dimension into the number of the detection elements 16, setting is performed so as to open the virtual mask for the number. Thus, the user can specify the opening dimension of the virtual mask with the feeling similar to the conventional operation of specifying a slit width of a rear optical receiving slit. Also, in the actual operation, the user specifies the opening width Lw and opening height Lh of the virtual mask using the input operation section 24 and then depresses a "registration" button in the figure (clicks it with a mouse or the like). Then, the virtual mask 31 is set on the detection surface 17 of the detector 15 according to the opening condition specified by the user.

Figure 5:
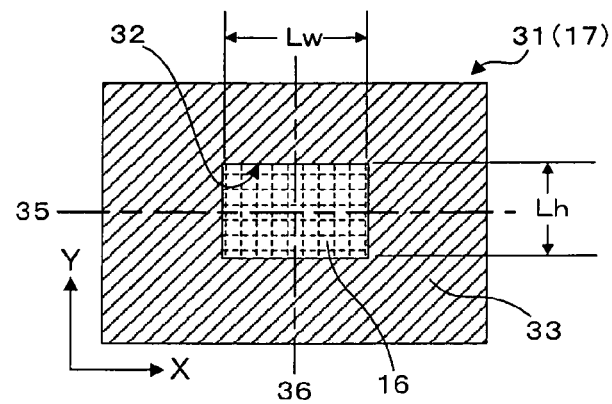
FIG. 5 is a diagram illustrating a state of setting the virtual mask on the detection surface of the detector.

Namely, as illustrated in FIG. 5, on the detection surface 17, with positions of a horizontal reference line 35 and a vertical reference line 36 that orthogonally cross at the center of the detection surface 17 as references, the virtual mask 31 is set by the opening width Lw and the opening height Lh specified by the user. At the time, the opening width Lw specified by the user is defined by the equal dimension horizontally with the vertical reference line 36 as the center in the X direction. Also, the opening height Lh specified by the user is defined by the equal dimension vertically with the horizontal reference line 35 as the center in the Y direction.

5. Relationship Between Opening Condition of Virtual Mask and Signal Processing Subsequently, the relationship between the opening condition of the virtual mask and the signal processing will be described.

Figure 6:
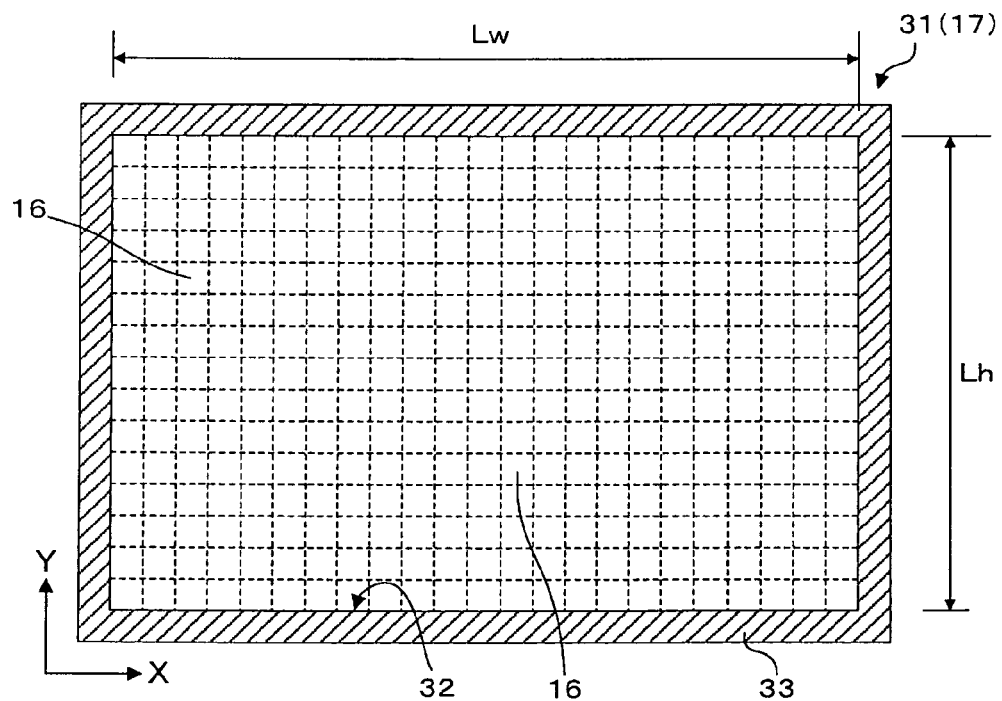
FIG. 6 is a schematic diagram illustrating a first setting example of an opening condition of the virtual mask.

FIG. 6 is a schematic diagram illustrating a first setting example of the opening condition of the virtual mask.

In this first setting example, the opening part 32 of the virtual mask 31 is set so as to be the maximum opening dimension (full open state). Specifically, the opening width Lw of the opening part 32 of the virtual mask 31 is set to the same dimension as the total width of the detection surface 17, and the opening height Lh of the opening part 32 is set to the same dimension as the total height of the detection surface 17. When the virtual mask 31 is set on the detection surface 17 under such an opening condition, all the detection elements 16 forming the detection surface 17 are disposed inside the opening part 32 of the virtual mask 31. In this case, the signal processing section 21 recognizes all the detection signals outputted from the respective detection elements 16 forming the detection surface 17 as valid signals and performs prescribed signal processing.

Figure 7:
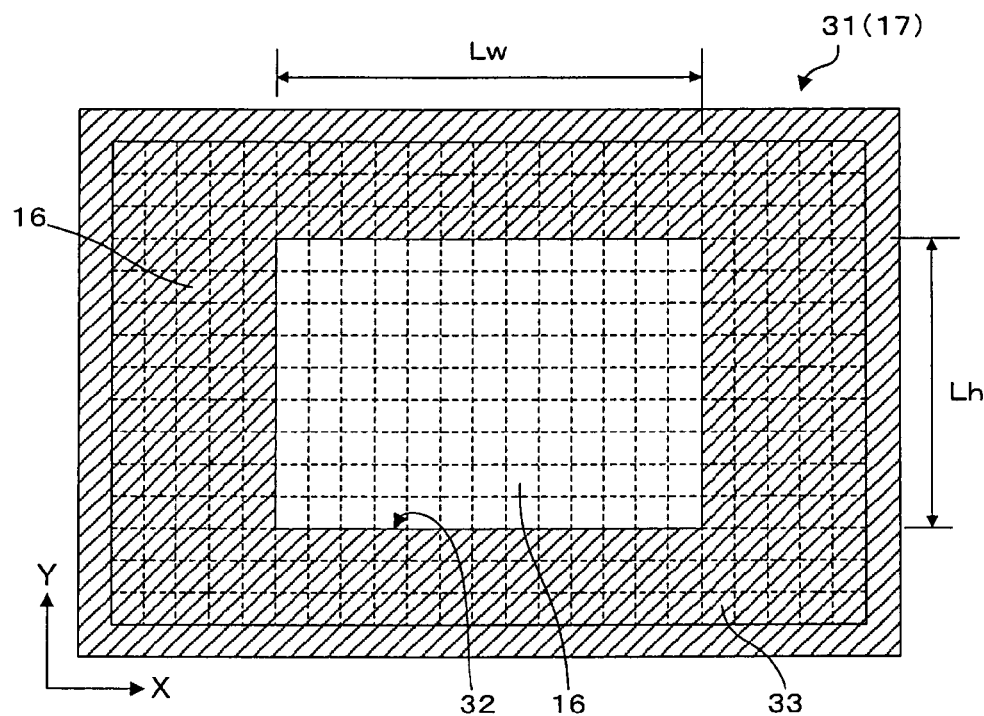
FIG. 7 is a schematic diagram illustrating a second setting example of the opening condition of the virtual mask.

FIG. 7 is a schematic diagram illustrating a second setting example of the opening condition of the virtual mask.

In this second setting example, the opening width Lw of the opening part 32 of the virtual mask 31 is set to the dimension shorter than the total width of the detection surface 17, and the opening height Lh of the opening part 32 is set to the dimension shorter than the total height of the detection surface 17. Specifically, the opening condition of the virtual mask is set to reduce the overall opening dimension of the virtual mask 31, thereby disposing only the part near the center of the detection surface 17 inside the opening part 32 of the virtual mask 31. Under this setting condition, the detection elements 16 positioned on the outer side of the opening part 32 of the virtual mask 31 are covered with the shield part 33 of the virtual mask 31.

When the opening condition of the virtual mask is set in this way, the signal processing section 21 recognizes the detection signals outputted from the detection elements 16 inside the opening part 32 of the virtual mask 31 as valid signals and the detection signals outputted from the other detection elements 16 as invalid signals. Thus, in the signal processing section 21, the signal processing is performed only for the detection signals outputted from the detection elements 16 inside the opening part 32 of the virtual mask 31. Also, in the signal processing section 21, as means of choosing the detection signals to be the object of the signal processing according to the opening condition of the virtual mask, for instance, a filter circuit or the like may be used to let the detection signals associated with the position information related to the detection elements 16 inside the opening part 32 of the virtual mask 31 pass through and intercepting the passing of the other detection signals.

Figure 8:
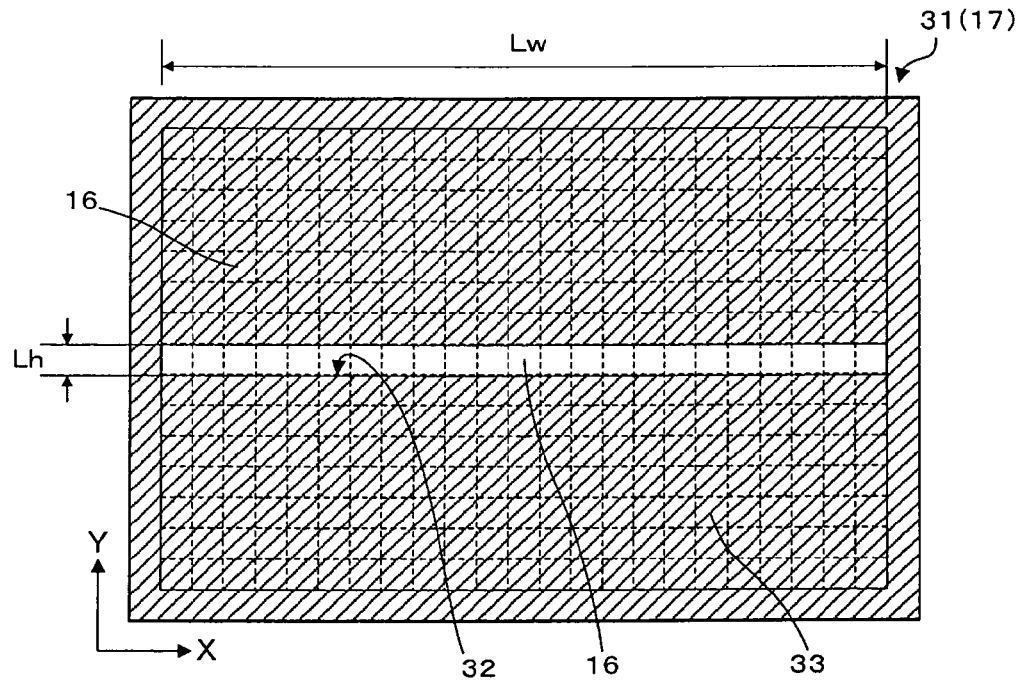
FIG. 8 is a schematic diagram illustrating a third setting example of the opening condition of the virtual mask.

FIG. 8 is a schematic diagram illustrating a third setting example of the opening condition of the virtual mask.

In this third setting example, the opening width Lw of the opening part 32 of the virtual mask 31 is set to the same dimension as the total width of the detection surface 17, and the opening height Lh of the opening part 32 is set to the dimension shorter than the total height of the detection surface 17. Specifically, the opening condition of the virtual mask is set so as to open only the center part in the Y direction of the detection surface 17 and to open over the total width of the detection surface 17 in the X direction so that the opening shape of the virtual mask 31 becomes a horizontally long slit shape as a whole. Under this setting condition, the detection elements 16 positioned on the upper side and on the lower side of the opening part 32 of the virtual mask 31 are covered with the shield part 33 of the virtual mask 31.

Figure 9:
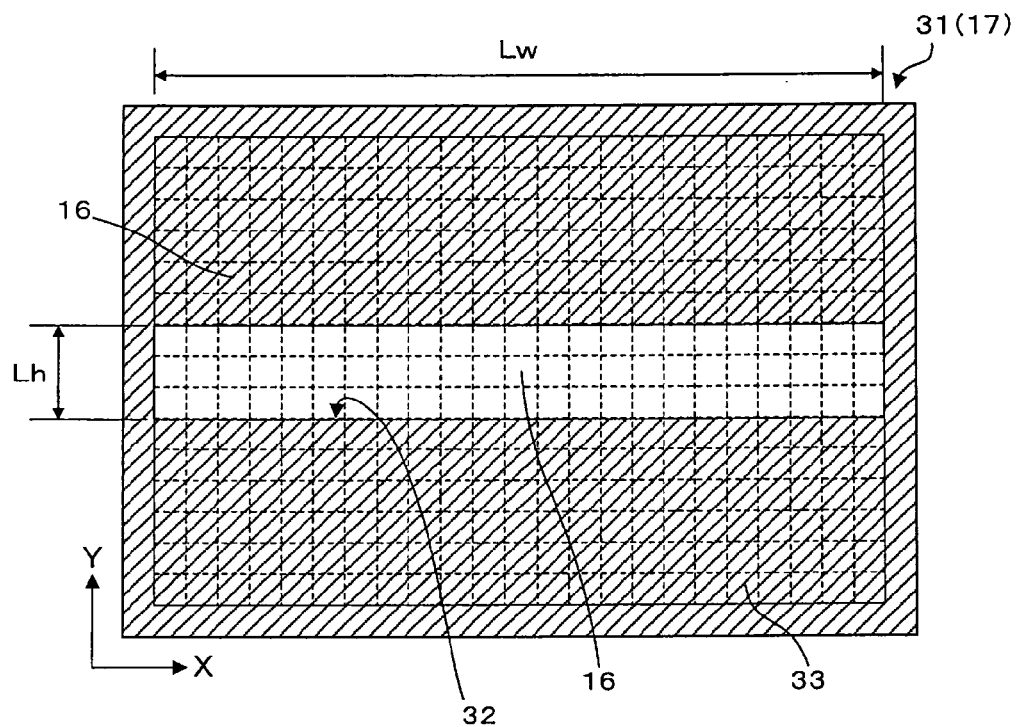
FIG. 9 is a schematic diagram illustrating a modification of the third setting example of the opening condition of the virtual mask.

When the opening condition of the virtual mask is set in this way, the signal processing section 21 similarly recognizes the detection signals outputted from the detection elements 16 inside the opening part 32 of the virtual mask 31 as valid signals and the detection signals outputted from the other detection elements 16 as invalid signals. Thus, in the signal processing section 21, the signal processing is performed only for the detection signals outputted from the detection elements 16 inside the opening part 32 of the virtual mask 31. Therefore, compared to the case of the first setting example illustrated in FIG. 6, since the opening dimension in the Y direction of the opening part 32 is reduced, the measurement resolution in the Y direction can be raised for that. Also, as a modification of the third setting example, by changing (increasing, in the illustrated example) the opening height Lh of the opening part 32 of the virtual mask 31 as illustrated in FIG. 9, the measurement resolution in the Y direction can be freely changed (adjusted).

Figure 10:
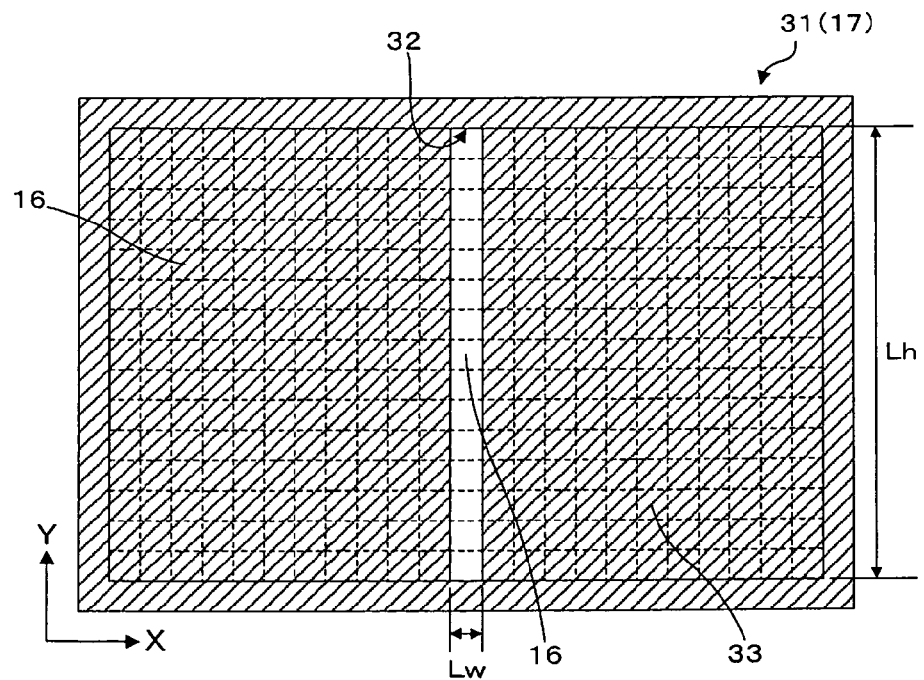
FIG. 10 is a schematic diagram illustrating a fourth setting example of the opening condition of the virtual mask.

FIG. 10 is a schematic diagram illustrating a fourth setting example of the opening condition of the virtual mask.

In this fourth setting example, the opening width Lw of the opening part 32 of the virtual mask 31 is set to the dimension shorter than the total width of the detection surface 17, and the opening height Lh of the opening part 32 is set to the same dimension as the total height of the detection surface 17. Specifically, the opening condition of the virtual mask is set so as to open only the center part in the X direction of the detection surface 17 and to open over the total height of the detection surface 17 in the Y direction so that the opening shape of the virtual mask 31 becomes a vertically long slit shape as a whole. Under this setting condition, the detection elements 16 positioned on the left side and on the right side of the opening part 32 of the virtual mask 31 are covered with the shield part 33 of the virtual mask 31.

Figure 11:
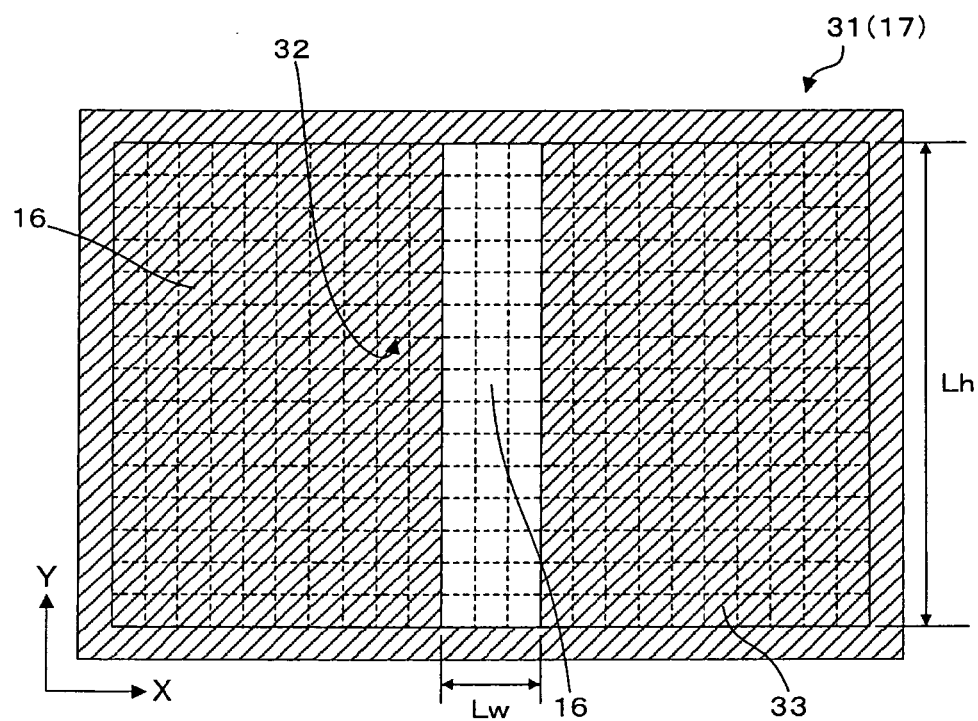
FIG. 11 is a schematic diagram illustrating a modification of the fourth setting example of the opening condition of the virtual mask.

When the opening condition of the virtual mask is set in this way, the signal processing section 21 similarly recognizes the detection signals outputted from the detection elements 16 inside the opening part 32 of the virtual mask 31 as valid signals and the detection signals outputted from the other detection elements 16 as invalid signals. Thus, in the signal processing section 21, the signal processing is performed only for the detection signals outputted from the detection elements 16 inside the opening part 32 of the virtual mask 31. Therefore, compared to the case of the first setting example illustrated in FIG. 6, since the opening dimension in the X direction of the opening part 32 is reduced, the measurement resolution in the X direction can be raised for that. Also, as a modification of the fourth setting example, by changing (increasing, in the illustrated example) the opening width Lw of the opening part 32 of the virtual mask 31 as illustrated in FIG. 11, the measurement resolution in the X direction can be freely changed (adjusted).

Figure 12:
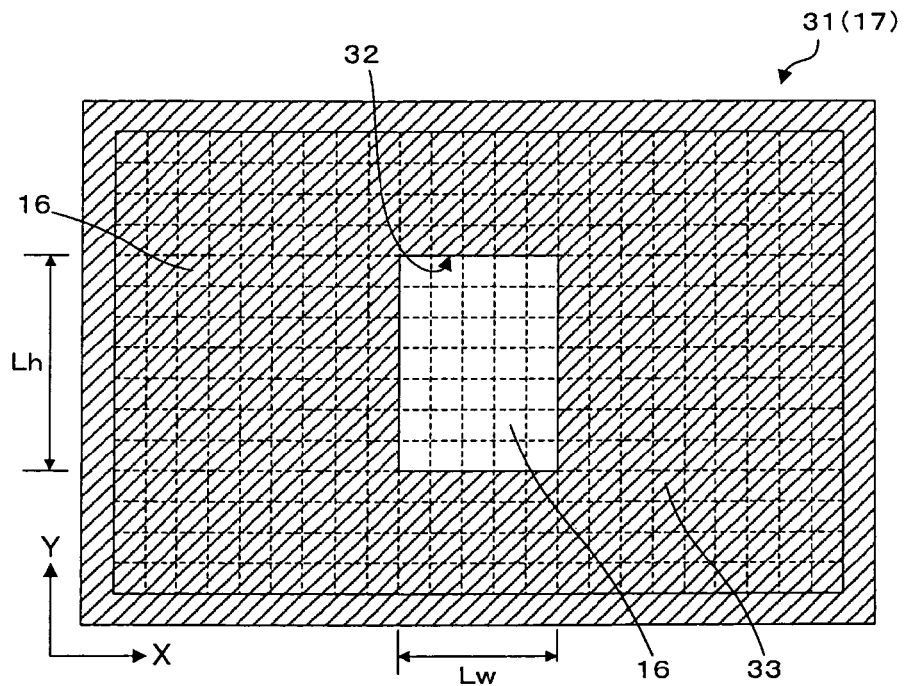
FIG. 12 is a schematic diagram illustrating a fifth setting example of the opening condition of the virtual mask.

FIG. 12 is a schematic diagram illustrating a fifth setting example of the opening condition of the virtual mask.

In this fifth setting example, similarly to the second setting example, the opening width Lw of the opening part 32 of the virtual mask 31 is set to the dimension shorter than the total width of the detection surface 17, and the opening height Lh of the opening part 32 is set to the dimension shorter than the total height of the detection surface 17.

When the opening condition of the virtual mask is set in this way, the signal processing section 21 similarly recognizes the detection signals outputted from the detection elements 16 inside the opening part 32 of the virtual mask 31 as valid signals and the detection signals outputted from the other detection elements 16 as invalid signals. Thus, in the signal processing section 21, the signal processing is performed only for the detection signals outputted from the detection elements 16 inside the opening part 32 of the virtual mask 31.

6. Second Example of Setting Screen of Virtual Mask

Figure 13:
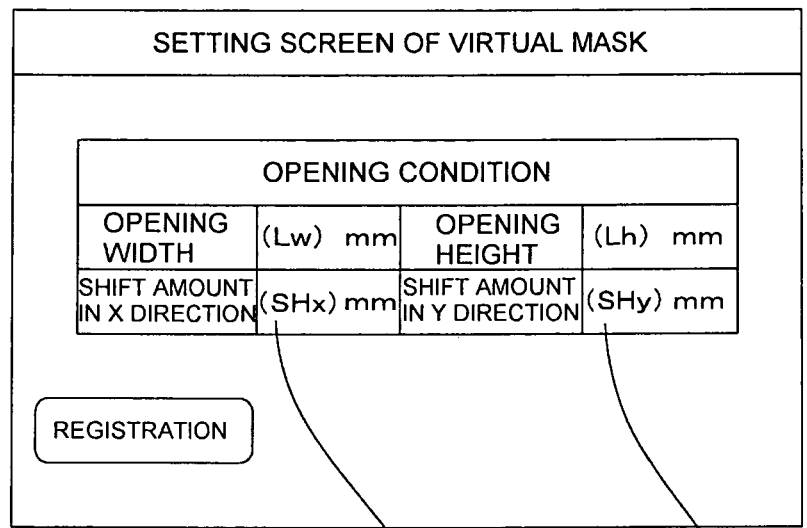
FIG. 13 is a diagram illustrating a second example of the setting screen of the virtual mask displayed on the monitor by the virtual mask setting section.
Figure 13:
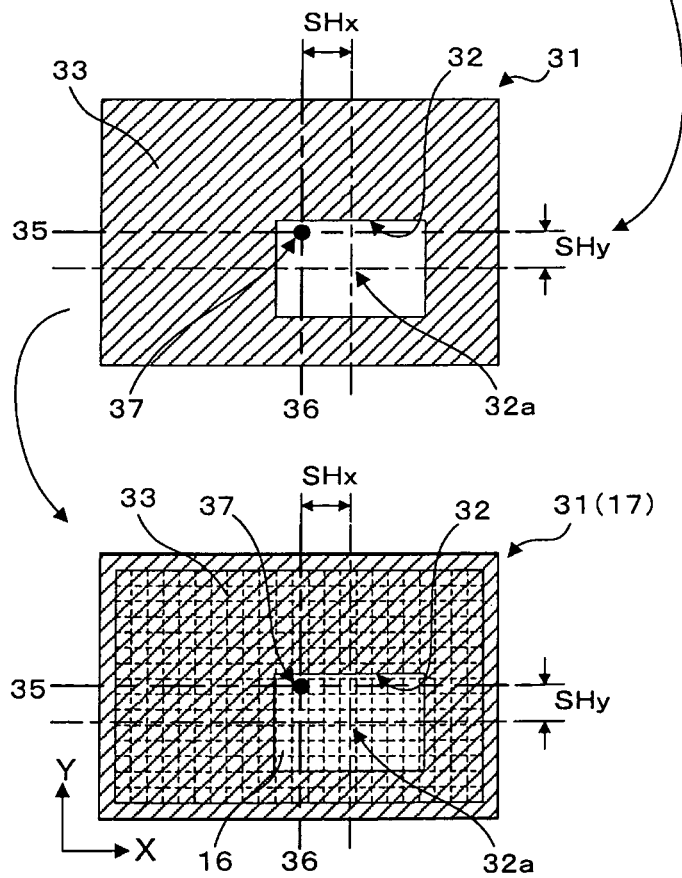

FIG. 13 is a diagram illustrating a second example of the setting screen of the virtual mask displayed on the monitor by the virtual mask setting section. On the setting screen of the virtual mask shown in the figure, as the opening condition of the virtual mask that can be set in the virtual mask setting section 26, in addition to the opening dimension (opening width Lw, opening height Lh) of the virtual mask, an opening center position of the virtual mask can be set by specifying shift amounts SHx and SHy. The opening center position of the virtual mask means a center position 32a of the opening part 32 of the virtual mask 31. The setting of the opening center position of the virtual mask can be specified independently in the X direction and the Y direction with a position of an intersection 37 of the horizontal reference line 35 and the vertical reference line 36 that cross at the center of the detection surface 17 as a reference. Also, on the setting screen of the virtual mask, similarly to the opening width Lw and the opening height Lh of the virtual mask, the shift amount SHx in the X direction and the shift amount SHy in the Y direction can be specified in millimeters, respectively.

The shift amount SHx in the X direction specifies how much the center position 32a of the opening part 32 of the virtual mask 31 is to be shifted in which of left and right directions by a numerical value, with the position of the intersection 37 as a reference. Namely, in the X direction of the detection surface 17, the center position 32a of the opening part 32 is defined by the shift amount SHx from the intersection 37. Thus, when the numerical value of the shift amount SHx is specified as zero, the center position 32a of the opening part 32 in the X direction is set at the position of the intersection 37. Also, when the numerical value of the shift amount SHx is specified by a positive value, the center position 32a of the opening part 32 in the X direction is set at a position shifted by the specified shift amount SHx to the right side of the position of the intersection 37. Also, when the numerical value of the shift amount SHx is specified by a negative value, the center position 32a of the opening part 32 in the X direction is set at a position shifted by the specified shift amount SHx to the left side of the position of the intersection 37.

The shift amount SHy in the Y direction specifies how much the center position 32a of the opening part 32 of the virtual mask 31 is to be shifted in which of upper and lower directions by a numerical value, with the position of the intersection 37 as a reference. Namely, in the Y direction of the detection surface 17, the center position 32a of the opening part 32 is defined by the shift amount SHy from the intersection 37. Thus, when the numerical value of the shift amount SHy is specified as zero, the center position 32a of the opening part 32 in the Y direction is set at the position of the intersection 37. Also, when the numerical value of the shift amount SHy is specified by a positive value, the center position 32a of the opening part 32 in the Y direction is set at a position shifted by the specified shift amount SHy to the upper side of the position of the intersection 37. Also, when the numerical value of the shift amount SHy is specified by a negative value, the center position 32a of the opening part 32 in the Y direction is set at a position shifted by the specified shift amount SHy to the lower side of the position of the intersection 37.

Next, the relationship between the opening condition of the virtual mask and the signal processing will be described.

Figure 14:
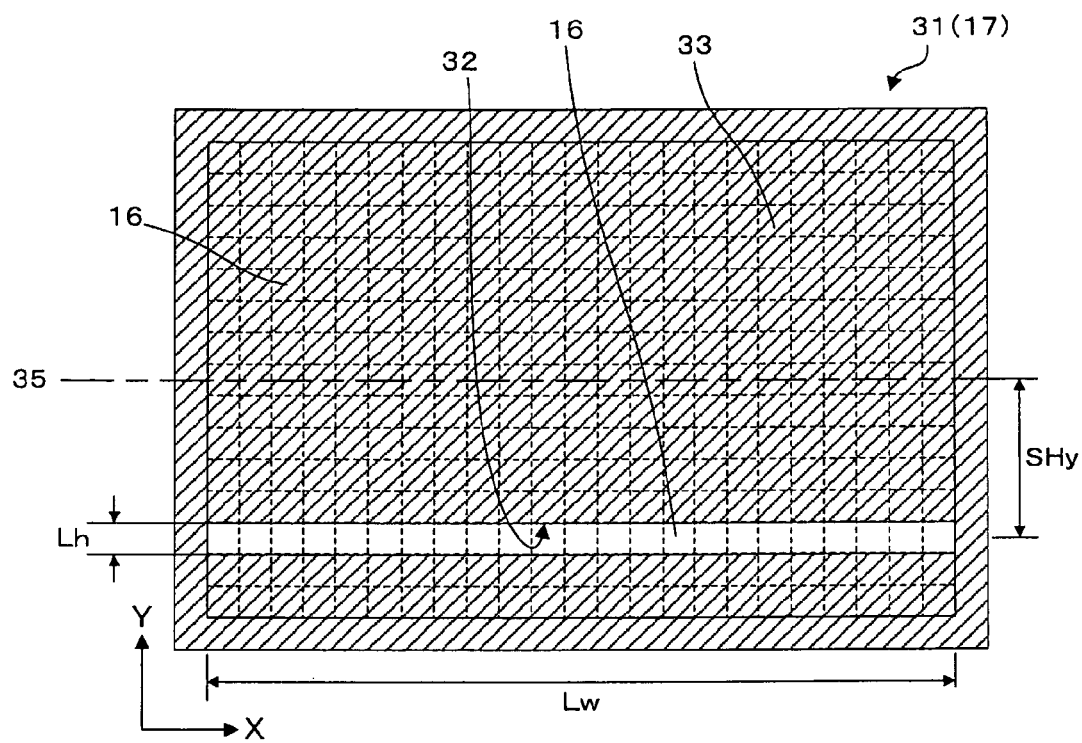
FIG. 14 is a schematic diagram illustrating a sixth setting example of the opening condition of the virtual mask.

FIG. 14 is a schematic diagram illustrating a sixth setting example of the opening condition of the virtual mask.

In this sixth setting example, regarding the opening dimension of the opening part 32 of the virtual mask 31, similarly to the third setting example illustrated in FIG. 8, the opening width Lw is set to the same dimension as the total width of the detection surface 17, and the opening height Lh of the opening part 32 is set to the dimension shorter than the total height of the detection surface 17. Therefore, the opening shape of the virtual mask 31 is the horizontally long slit shape as a whole. Also, in the sixth setting example, the shift amount SHx (not shown in the figure) in the X direction is set to zero, and the shift amount SHy in the Y direction is set at the negative value. Thus, the center position of the opening part 32 of the virtual mask 31 is shifted to the lower side of the horizontal reference line 35.

When the opening center position of the virtual mask is shifted in the Y direction and set by specifying the shift amount SHy in this way, the shift of the incident position of the X-rays can be coped with, without mechanically moving the opening/closing center position of the rear optical receiving slit as before. Hereinafter, concrete descriptions will be given.

Figure 15:
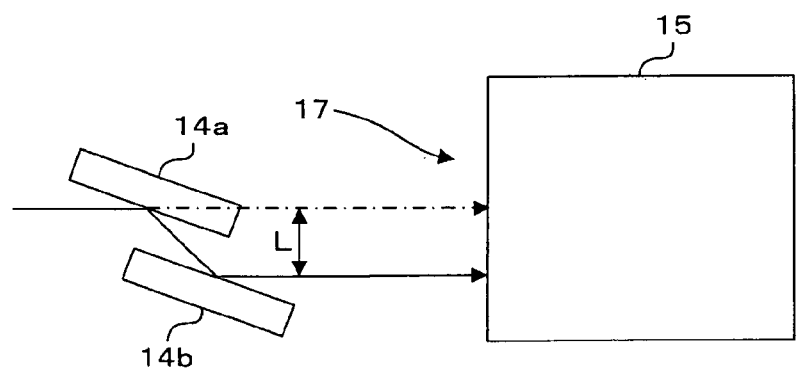
FIG. 15 is a diagram describing a shift of an incident position of X-rays when installing a monochromator crystal in the measurement optical system.

First, in the X-ray diffraction apparatus, as illustrated in FIG. 15 for instance, there is the case of reflecting the X-rays by respective monochromator crystals 14a and 14b and improving parallelism of the X-rays and wavelength selectivity by installing the two monochromator crystals 14a and 14b in the measurement optical system, in order to raise the measurement resolution. In that case, since the path of the X-rays varies before and after installing the monochromator crystals 14a and 14b, the position of the X-rays made incident on the detection surface 17 of the detector 15 is changed. Specifically, the position of the X-rays made incident on the detection surface 17 is shifted in the vertical direction.

Figure 29A:
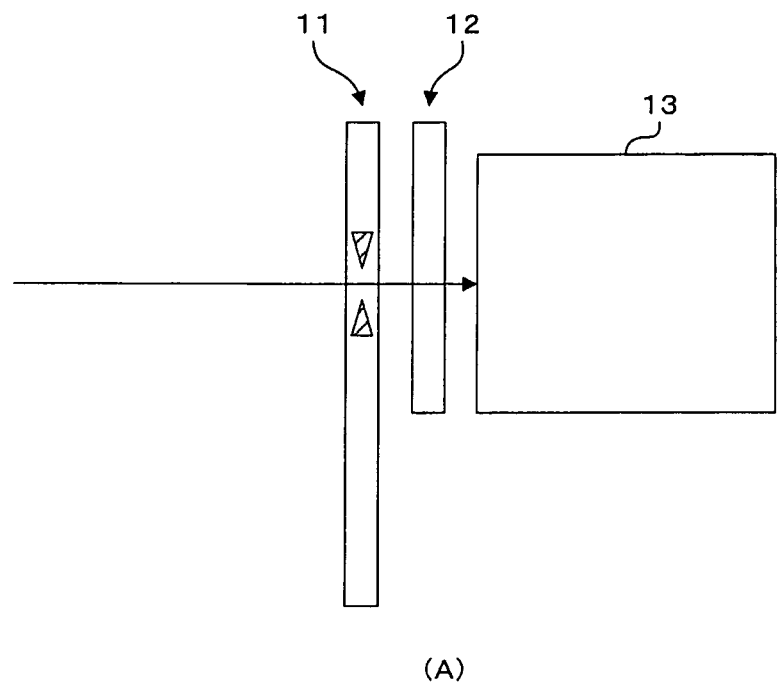
FIGS. 29A and 29B are diagrams illustrating states of shifting an opening/closing center position of the rear optical receiving slit according to the shift of the incident position of the X-rays when installing the monochromator crystal in the measurement optical system.
Figure 29B:
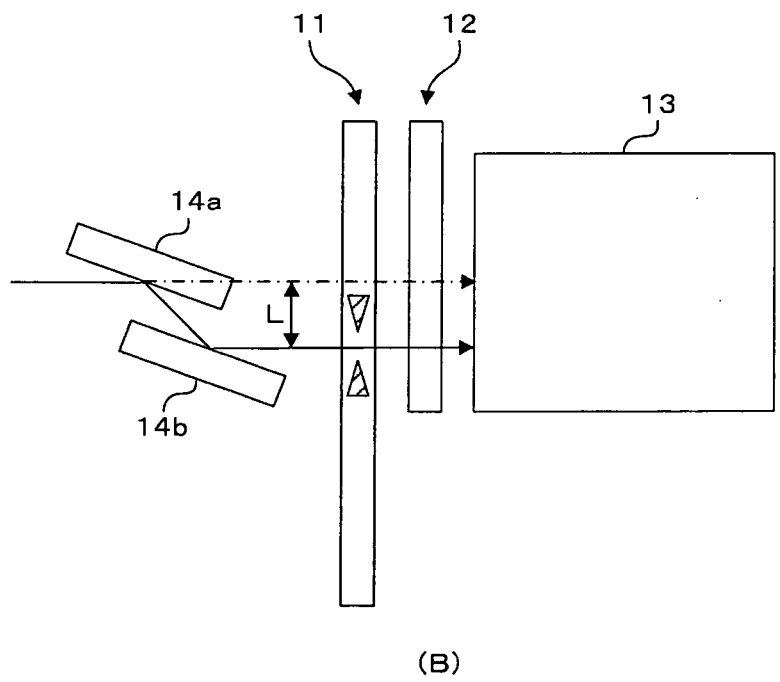

In such a case, in a conventional X-ray diffraction apparatus, as illustrated in FIG. 29, it is needed to match an opening/closing center position of the rear optical receiving slit 11 with the incident position of the X-rays by mechanically moving the rear optical receiving slit 11 in the Y direction according to the shift amount L of the incident position of the X-rays to the detection surface of the detector 13. In contrast, in the X-ray diffraction apparatus according this embodiment, by specifying the shift amount SHy in the Y direction by either positive or negative value on the setting screen illustrated in FIG. 13, the center position 32a of the opening part 32 of the virtual mask 31 can be freely shifted in the Y direction. Therefore, when the incident position of the X-rays to the detection surface 17 is changed before and after installing the monochromator crystals 14a and 14b, by specifying the shift amount SHy in the Y direction according to the shift amount L of the incident position of the X-rays before and after the change, the opening center position of the virtual mask can be matched with the incident position of the X-rays. Thus, the shift of the incident position of the X-rays can be coped with, without mechanically moving the rear optical receiving slit as before.

Also, while the case of shifting and setting the opening center position of the virtual mask is described here, other than that, it is possible to shift and set the opening center position of the virtual mask in the X direction or shift and set the opening center position of the virtual mask in both of the X direction and the Y direction, although not shown in the figure. Also, as a function of the virtual mask setting section 26, the configuration may be such that only one of the shift amount SHx in the X direction and the shift amount SHy in the Y direction can be specified (set).

Also, as an additional function of the virtual mask setting section 26, a configuration may be adopted such that, in addition to the opening condition of the virtual mask described above, for instance, "the number of openings of the virtual mask", "the opening shape of the virtual mask" or "the inclination angle of the opening of the virtual mask" or the like can be set. "The number of openings of the virtual mask" means the number of the opening parts 32 to be set to the virtual mask 31. "The opening shape of the virtual mask" means a shape of the opening part 32 to be set to the virtual mask 31. "The inclination angle of the opening of the virtual mask" means an inclination angle of the opening part 32 to be set to the virtual mask 31.

(Regarding the Number of Openings of Virtual Mask)

Regarding the number of the openings of the virtual mask, the configuration may be such that the number of openings can be specified by a numerical value on the setting screen of the virtual mask displayed on the monitor 23 by the virtual mask setting section 26. Also, for the number of the openings of the virtual mask, the configuration may be such that an initial value is "1" and a user can change the number of the openings of the virtual mask from the initial value "1" to a numerical value of "2 or greater" as needed.

Figure 16:
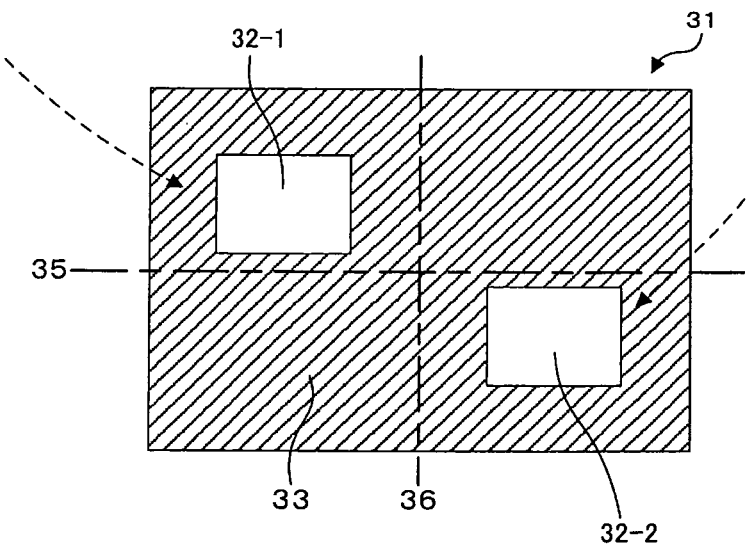
FIG. 16 is a schematic diagram illustrating the setting screen of the virtual mask and a seventh setting example of the opening condition based thereon.

FIG. 16 is a schematic diagram illustrating a setting screen of the virtual mask and a seventh setting example of the opening condition based on it.

On the setting screen of the virtual mask shown in the figure, the number of the openings of the virtual mask can be specified by a numerical value. In the seventh setting example, the number of the openings of the virtual mask is set at "2". Therefore, on the setting screen of the virtual mask, for the two opening parts 32-1 and 32-2, the opening condition of the virtual mask can be specified separately. Also, in the seventh setting example, regarding the first opening part 32-1, the opening dimension is set to Lw1 and Lh1 and the opening center position is set to SHx1 and SHy1. Also, regarding the second opening part 32-2, the opening dimension is set to Lw2 and Lh2 and the opening center position is set to SHx2 and SHy2.

When the opening condition of the virtual mask is set in this way, the signal processing section 21 recognizes the detection signals outputted from the detection elements 16 inside the first opening part 32-1 of the virtual mask 31 and the detection signals outputted from the detection elements 16 inside the second opening part 32-2 as valid signals respectively, and recognizes the detection signals outputted from the other detection elements 16 as invalid signals. Therefore, in the signal processing section 21, the signal processing is performed only for the detection signals outputted from the detection elements 16 inside the first opening part 32-1 of the virtual mask 31 and the detection signals outputted from the detection elements 16 inside the second opening part 32-2. Thus, the measurement result of the X-ray diffraction can be displayed on the monitor 23 for each of the respective opening parts 32-1 and 32-2 of the virtual mask 31.

Figure 17A:
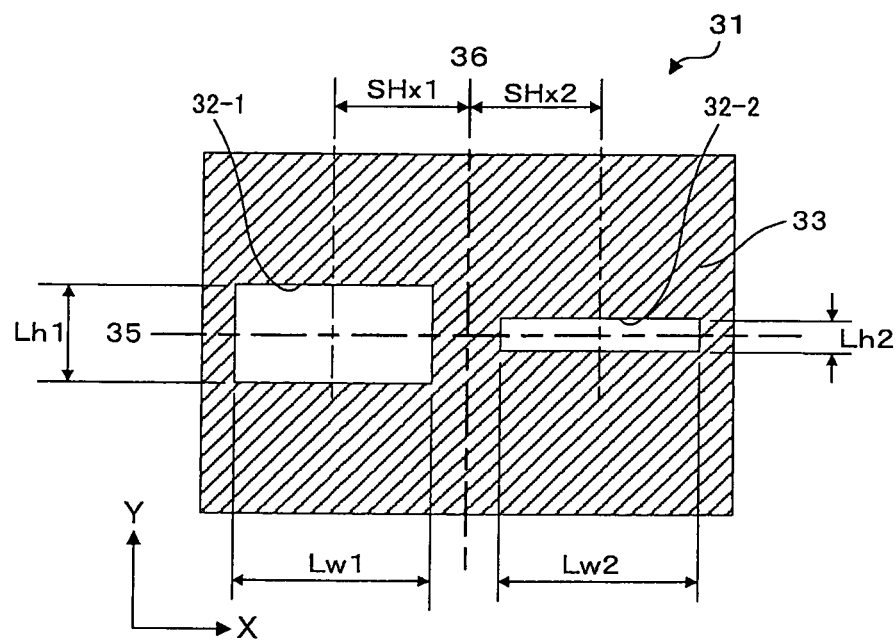
FIGS. 17A and 17B are schematic diagrams illustrating a modification of the seventh setting example of the opening condition of the virtual mask.

Also, as a modification of the seventh setting example, by changing the specification of the opening dimension (Lw1, Lh1) and the opening center position (SHx1, SHy1) for the first opening part 32-1 and the specification of the opening dimension (Lw2, Lh2) and the opening center position (SHx2, SHy2) for the second opening part 32-2, the virtual mask 31 can be set under the opening condition as illustrated in FIG. 17(A). In this setting example, the shield part 33 is sectioned into two left and right areas with the vertical reference line 36 as a boundary. Then, in the area on the left side, the first opening part 32-1 is set under the condition that the opening dimension is the opening height Lh1 and the opening width Lw1 and the condition that the opening center position is at the shift amount SHx1, SHy1 (not shown in the figure), as the opening condition of the virtual mask 31. Also, in the area on the right side, the second opening part 32-2 is set under the condition that the opening dimension is the opening height Lh2 and the opening width Lw2 and the condition that the opening center position is at the shift amount SHx2, SHy2 (not shown in the figure), as the opening condition of the virtual mask 31. Among them, the opening height Lh1 of the first opening part 32-1 is specified by the dimension greater than the opening height Lh2 of the second opening part 32-2. Also, the opening width Lw1 of the first opening part 32-1 and the opening width Lw2 of the second opening part 32-2 are both specified by the dimension slightly shorter than a half of the total width of the detection surface 17. The shift amounts SHx1 and SHx2 in the X direction are specified by numerical values which have the same absolute value and are differently positive and negative. Also, the shift amounts SHy1 and SHy2 in the Y direction are both specified by the numerical value of zero.

Figure 17B:
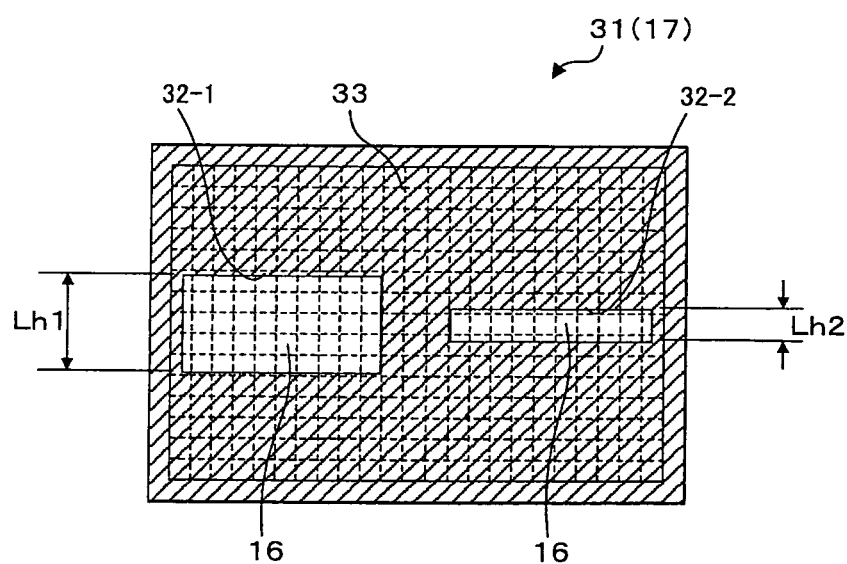

When the opening condition of the virtual mask is set in this way, as illustrated in FIG. 17(B), by differentiating the opening heights Lh1 and Lh2 of the respective opening parts 32-1 and 32-2 in the area on the left side and the area on the right side of the shield part 33, the measurement resolution of the measurement result obtained by signal-processing the detection signals outputted from the detection elements 16 inside the first opening part 32-1 in the signal processing section 21 and the measurement resolution of the measurement result obtained by signal-processing the detection signals outputted from the detection elements 16 inside the second opening part 32-2 in the signal processing section 21 become different. Therefore, the measurement results of the different measurement resolutions can be obtained by the measurement of one time.

Also, when the user sets the plurality of openings on the setting screen of the virtual mask, it is possible that respective opening positions overlap with each other or the like and interfere within a surface of the virtual mask 31 set on the detection surface 17. In such a case, for instance, it is desirable to adopt a configuration to notify the user of that effect by issuing alarm sound or voice guidance by a speaker or the like or displaying an alarm message or the like on the monitor 23.

Also, when setting the number of the openings of the virtual mask as the opening condition of the virtual mask, the configuration may be such that the detection surface 17 of the detector 15 is sectioned into two or sectioned into four with the horizontal reference line 35 or the vertical reference line 36 as a boundary, and the opening dimension and the opening position of the virtual mask can be individually set for each section area. Also, when sectioning the detection surface 17 into two or four in such a manner, the configuration may be such that, an initial condition is fixedly set for at least one of the opening dimension and the opening position of the virtual mask and the plurality of mask openings are set on the detection surface 17 according to the initial condition. Specifically, when sectioning the detection surface 17 into four for instance, the configuration may be such that the opening dimension of the virtual mask is fixedly set as the initial condition and the user can specify only the opening center position of the virtual mask on the setting screen. Also, the configuration may be such that the initial condition is fixedly set so that the opening center position of the virtual mask is the center of each section area and the user can specify only the opening dimension of the virtual mask on the setting screen.

Although the concrete setting screen of the virtual mask for "the opening shape of the virtual mask" and "the inclination angle of the opening of the virtual mask" is not illustrated, the virtual mask can be set under the opening condition as follows by receiving the specification of the user in the virtual mask setting section 26 for the opening conditions as well.

(Regarding Opening Shape of Virtual Mask)

Figure 18A:
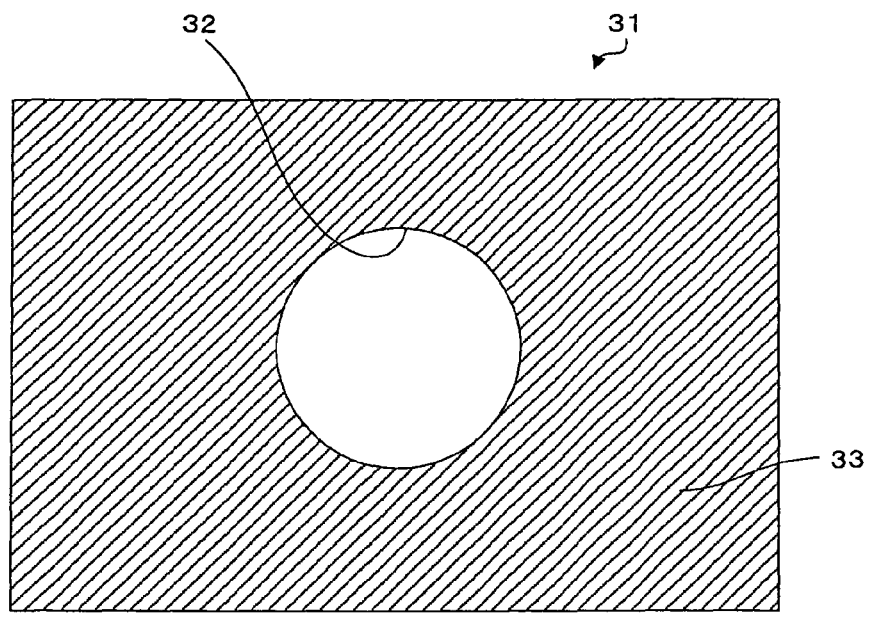
FIGS. 18A and 18B are schematic diagrams illustrating a setting example of an opening shape of the virtual mask.
Figure 18B:
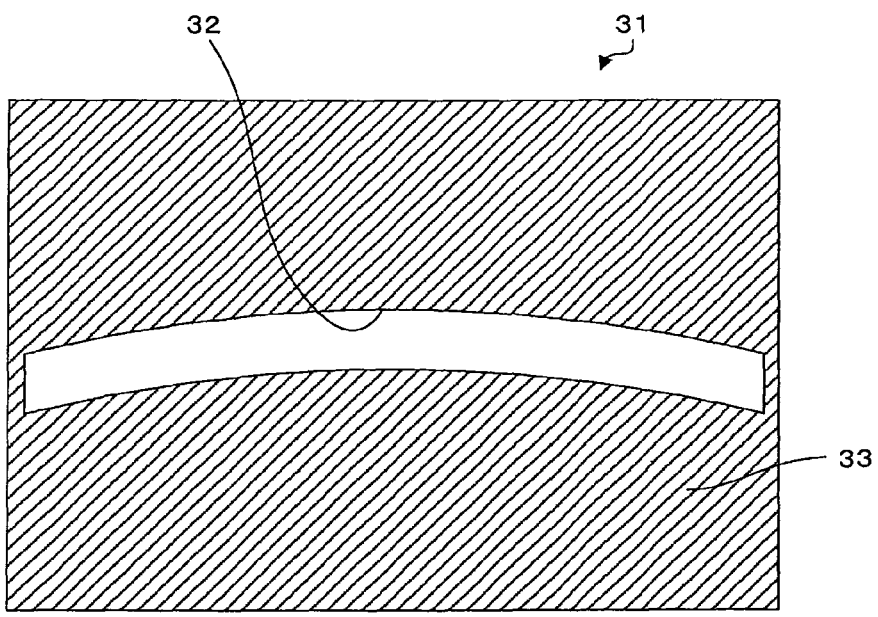

Namely, when the opening shape of the virtual mask can be set as one of the opening conditions of the virtual mask, for instance, the virtual mask 31 having a circular opening part 32 can be set as illustrated in FIG. 18(A), or the virtual mask 31 having a circular arcuate opening part 32 can be set as illustrated in FIG. 18(B). For the opening shape of the virtual mask, for instance, a rectangular opening shape is applied in initial setting, and it can be changed into an arbitrary shape according to user's desire. Also, by the configuration capable of setting the opening dimension and/or the opening center position of the virtual mask together with the opening shape of the virtual mask as the opening condition of the virtual mask, the virtual mask having a desired opening shape can be set in a desired dimension at a desired position within the surface of the detection surface 17.

(Inclination Angle of Opening of Virtual Mask)

Figure 19:
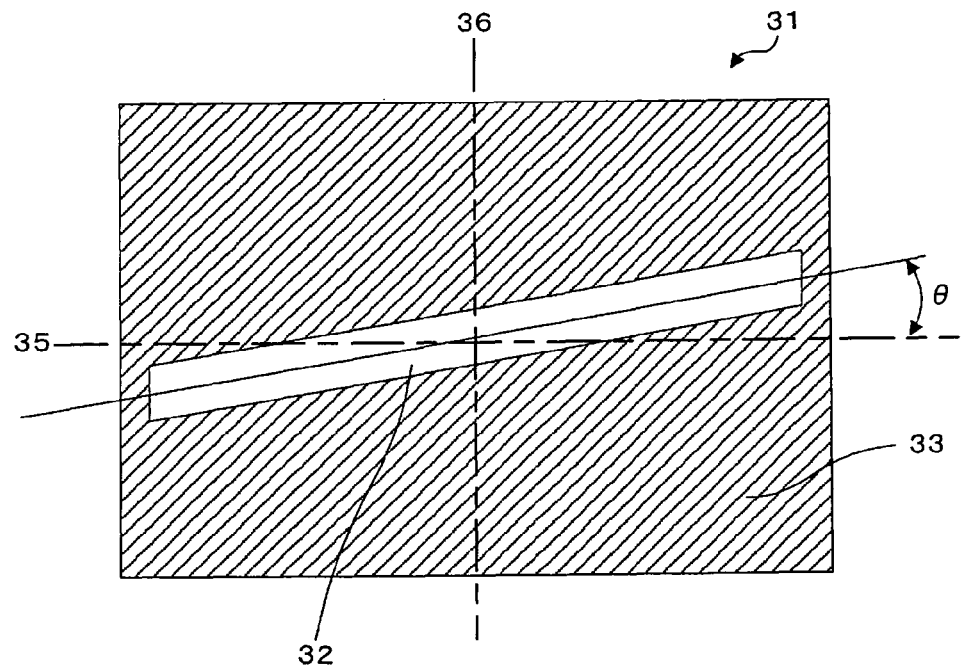
FIG. 19 is a schematic diagram illustrating a setting example of an inclination angle of an opening of the virtual mask.

In the case that the inclination angle of the opening of the virtual mask can be set as one of the opening conditions of the virtual mask, when the inclination angle is specified as "+10 degrees" for instance, as illustrated in FIG. 19, the opening part 32 of the virtual mask 31 can be set in the state of being inclined by $\theta=10$ degrees counterclockwise. The inclination angle of the opening of the virtual mask can be specified by the inclination angle of the opening part 32 to the horizontal reference line 35 (or the vertical reference line 36). Specifically, for instance, the condition that the inclination angle of the mask opening is 0 degree is the initial setting, the mask opening is set in the state of being inclined by a specified angle in a counterclockwise direction when the inclination angle is specified by a positive value, and the mask opening is set in the state of being inclined by a specified angle in a clockwise direction when the inclination angle is specified by a negative value.

According to the structure in which the inclination angle can be set in the opening of the virtual mask, the following countermeasure can be taken when the size of each detection element 16 is reduced for example in the future. Namely, when a sectional shape of the X-rays incident on the detection surface 17 is inclined due to the inclination of the sample stage 7 or the inclination of the surface of the sample S, the opening part 32 of the virtual mask 31 can be inclined without requiring a mechanical adjustment such as a sample stage 7, or as a preliminary adjustment before performing the mechanical positional adjustment.

7. Second Constitutional Example of X-Ray Diffraction Apparatus

Figure 20:
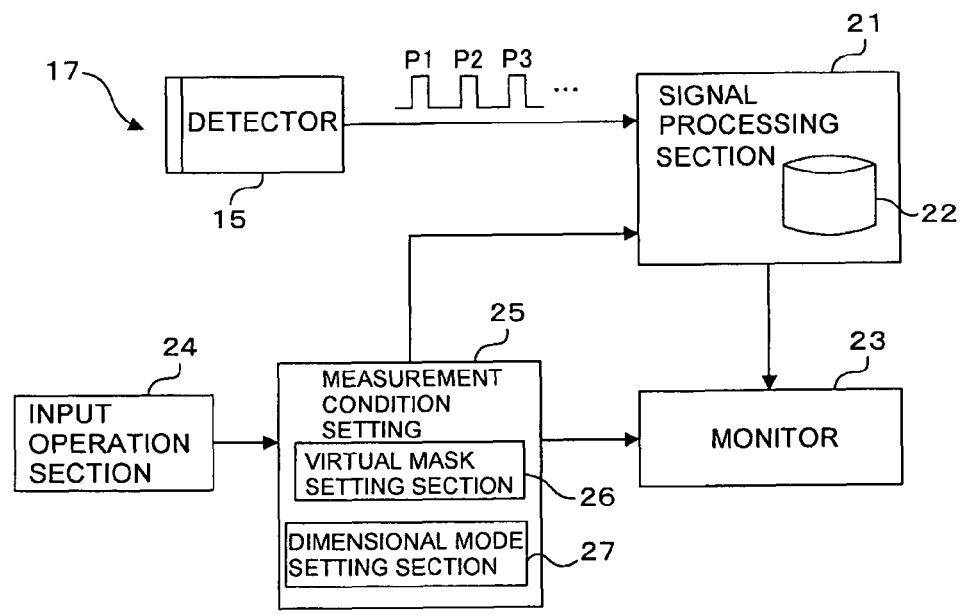
FIG. 20 is a functional block diagram illustrating a second constitutional example of the X-ray diffraction apparatus according to an embodiment of the present invention.

FIG. 20 is a functional block diagram illustrating a second constitutional example of the X-ray diffraction apparatus according to an embodiment of the present invention. In the configuration of the X-ray diffraction apparatus shown in the figure, the measurement condition setting section 25 includes a dimensional mode setting section 27 in addition to the virtual mask setting section 26. The dimensional mode setting section 27 sets a dimensional mode used for measuring the X-ray diffraction using the detector 15. As the dimensional mode that can be set in the dimensional mode setting section 27, there are three dimensional modes of "zero-dimensional mode", "one-dimensional mode" and "two-dimensional mode". The zero-dimensional mode is the dimensional mode not having the position resolution. The one-dimensional mode is the dimension mode having a one-dimensional position resolution. The two-dimensional mode is the dimensional mode having a two-dimensional position resolution. The dimensional mode setting section 27 sets the dimensional mode to be applied when measuring the X-ray diffraction by having the user specify one of the three dimensional modes using the input operation section 24.

The dimensional mode set based on an instruction of a user, is reflected on a processing form for applying processing to the detection signals outputted from the detection elements 16, which is the signals obtained when detecting the X-ray using the detector 15. Specifically, when the dimensional mode is set in zero-dimensional mode, processing is applied to the signal so as to integrate all detection signals of the detection elements 16 in the opening of the virtual mask set on the detection surface 17. Further, when the dimensional mode is set in one-dimensional mode, the detection signals of the detection elements 16 in the opening of the virtual mask set on the detection surface 17 are integrated and processed, for each row unit or column unit. Which of the raw unit or the column unit is selected for integrating the detection signals of the detection elements 16, is determined by selecting the X direction or the Y direction set in one-dimensional mode. When the two-dimensional mode is set, the detection signals of the detection elements 16 are processed, for each unit of the detection elements in the opening of the virtual mask set on the detection surface 17.

Hereinafter, when the opening condition of the virtual mask is set as in FIG. 7 and the dimensional mode is set under the setting condition, explanation is given for a processing manner performed by the signal processing section 21, applied to the detection signal outputted from the detector 15.

Figure 21:
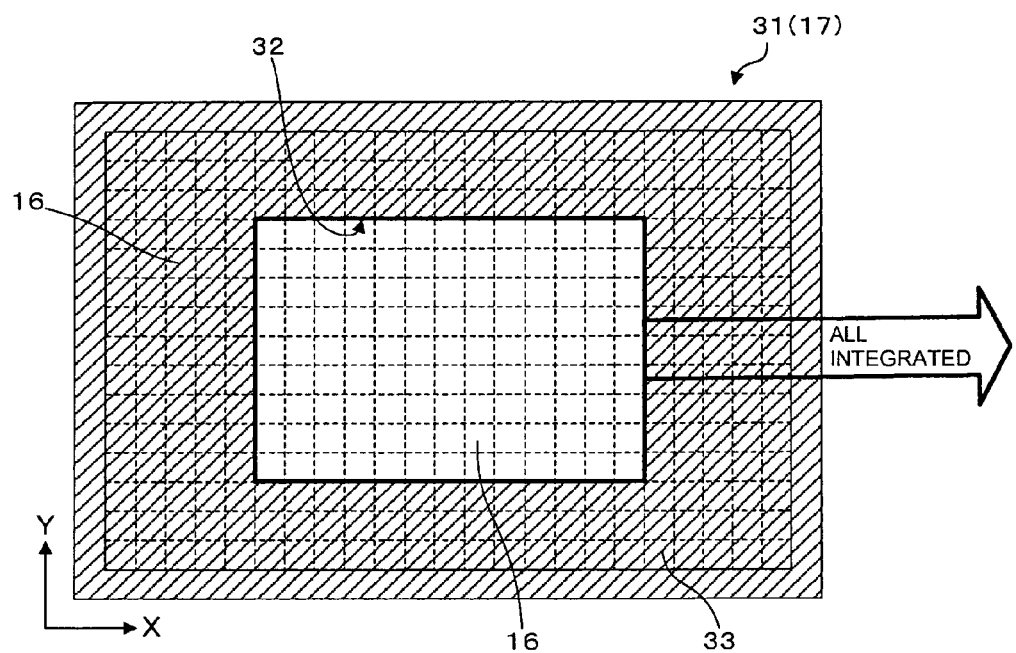
FIG. 21 is a schematic diagram illustrating one example of a measurement condition when setting a dimensional mode to a zero-dimensional mode.

When the dimensional mode is set to the zero-dimensional mode in the dimensional mode setting section 27, as illustrated in FIG. 21, the signal processing section 21 integrates all detection signals outputted from the detection elements 16 in the opening part 32 of the virtual mask 31. Thus, the measurement result is obtained, similarly to the case of using a zero-dimensional detector substantially.

Figure 22:
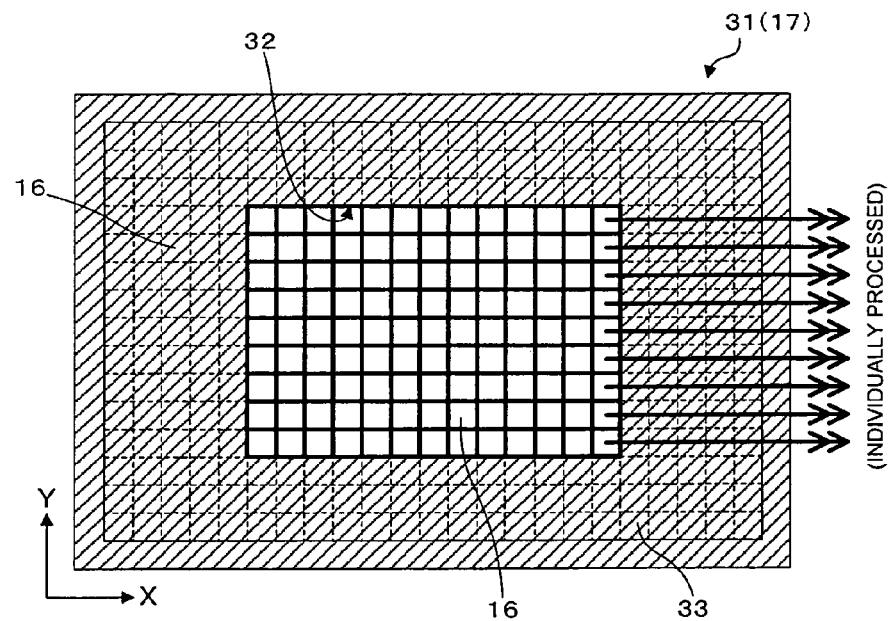
FIG. 22 is a schematic diagram illustrating one example of the measurement condition when setting the dimensional mode to a two-dimensional mode.

When the dimensional mode is set to the two-dimensional mode by the dimensional mode setting section 27, as illustrated in FIG. 22, the signal processing section 21 individually processes the detection signals, for each unit of the detection elements 16, which are the signals outputted from each detection element 16 in the opening part 32 of the virtual mask 31. Thus, the measurement result is obtained similarly to the case of substantially using a two-dimensional detector.

Figure 23:
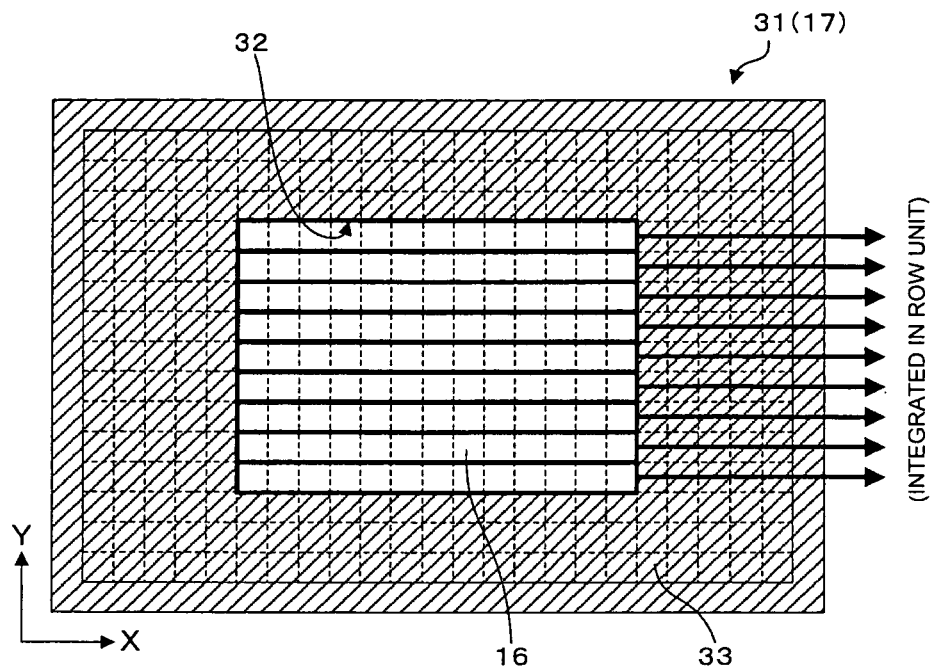
FIG. 23 is a schematic diagram illustrating one example of the measurement condition when setting the dimensional mode to a one-dimensional mode in Y direction.

When the dimensional mode is set to the one-dimensional mode in the Y direction in the dimensional mode setting section 27, as illustrated in FIG. 23, the signal processing section 21 integrates the detection signals, for each unit of the rows, which is the signals outputted from each detection element 16 in the opening part 32 of the virtual mask 31. Thus, the measurement result is obtained similarly to the case of using a one-dimensional detector in which line-shaped detection elements which are long substantially in the X direction, are arranged in the Y direction.

Figure 24:
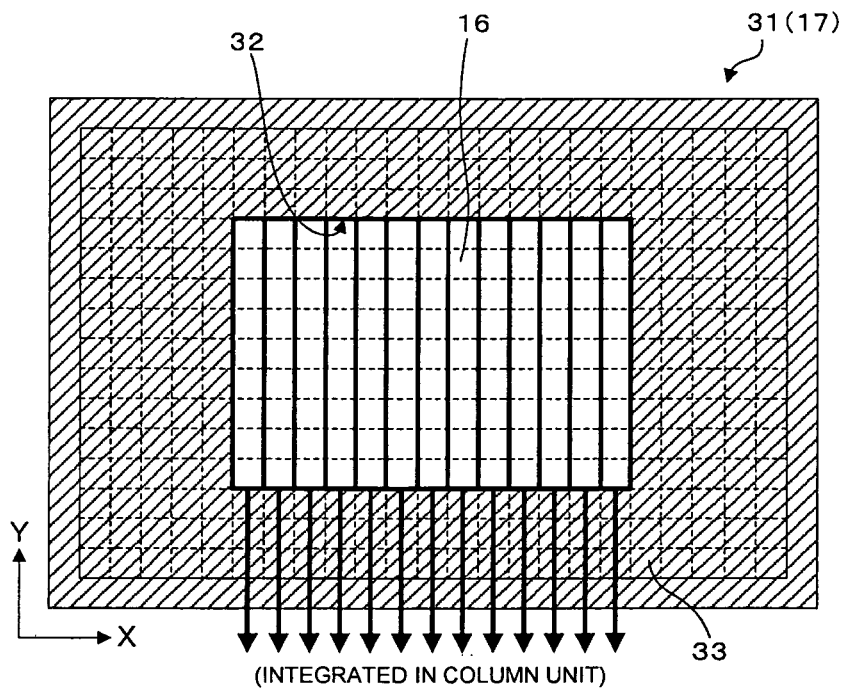
FIG. 24 is a schematic diagram illustrating one example of the measurement condition when setting the dimensional mode to a one-dimensional mode in X direction.

When, the dimensional mode setting section 27 sets the dimensional mode as one-dimensional mode in the X direction, as illustrated in FIG. 24, the signal processing section 21 integrates the detection signals in the unit of columns, which are the signals outputted from the detection elements 16 in the opening part 32 of the virtual mask 31. Thus, the measurement result is obtained similarly to the case of using a one-dimensional detector configured in which line-shaped detection elements which are long substantially in the Y direction, are arranged in the X direction.

Also, although not shown, when the opening condition of the virtual mask is set so that the whole body of the opening part 32 of the virtual mask 31 is small, compared with the dimensional mode of FIG. 21, the measurement resolution for detecting the X-rays in the zero-dimensional mode can be raised.

Figure 25:
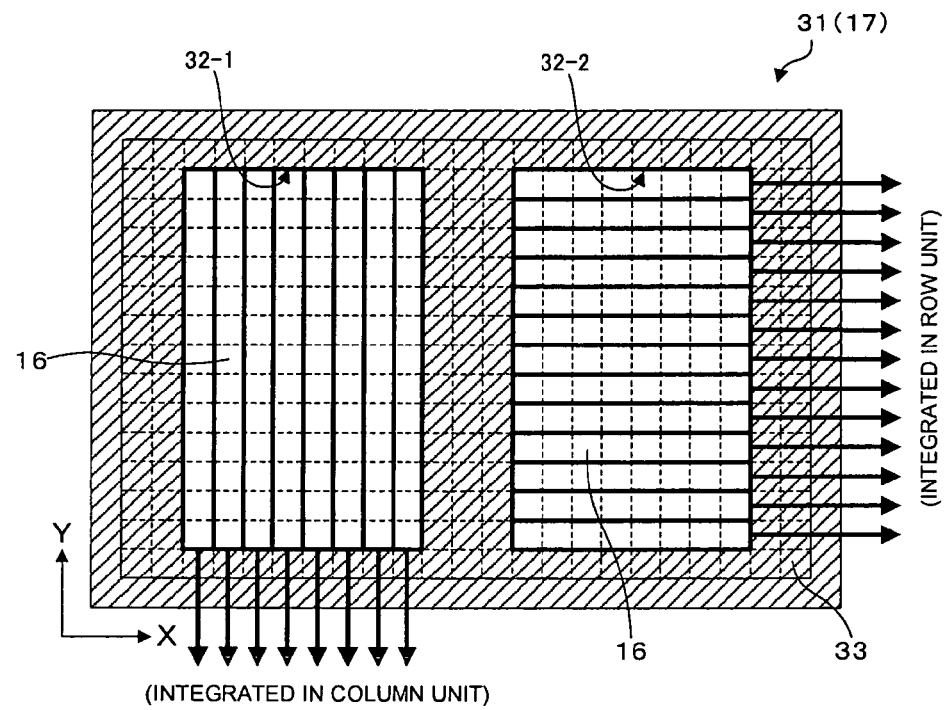
FIG. 25 is a schematic diagram illustrating a first application example of the measurement condition realized by combining setting of the virtual mask and setting of the dimensional mode.
Figure 26:
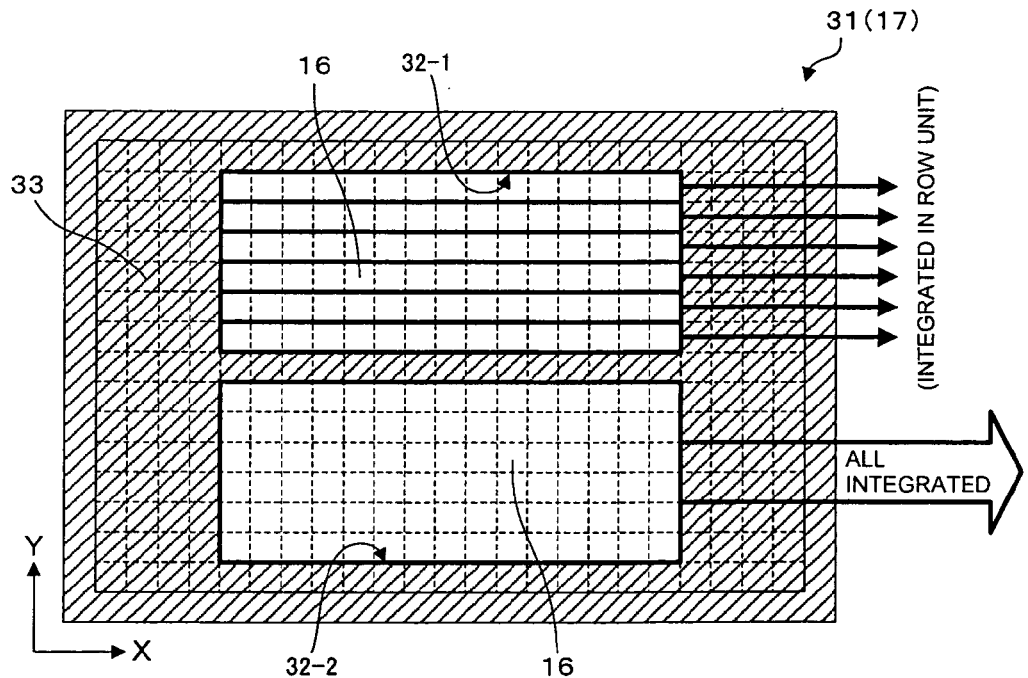
FIG. 26 is a schematic diagram illustrating a second application example of the measurement condition realized by combining the setting of the virtual mask and the setting of the dimensional mode.
Figure 27:
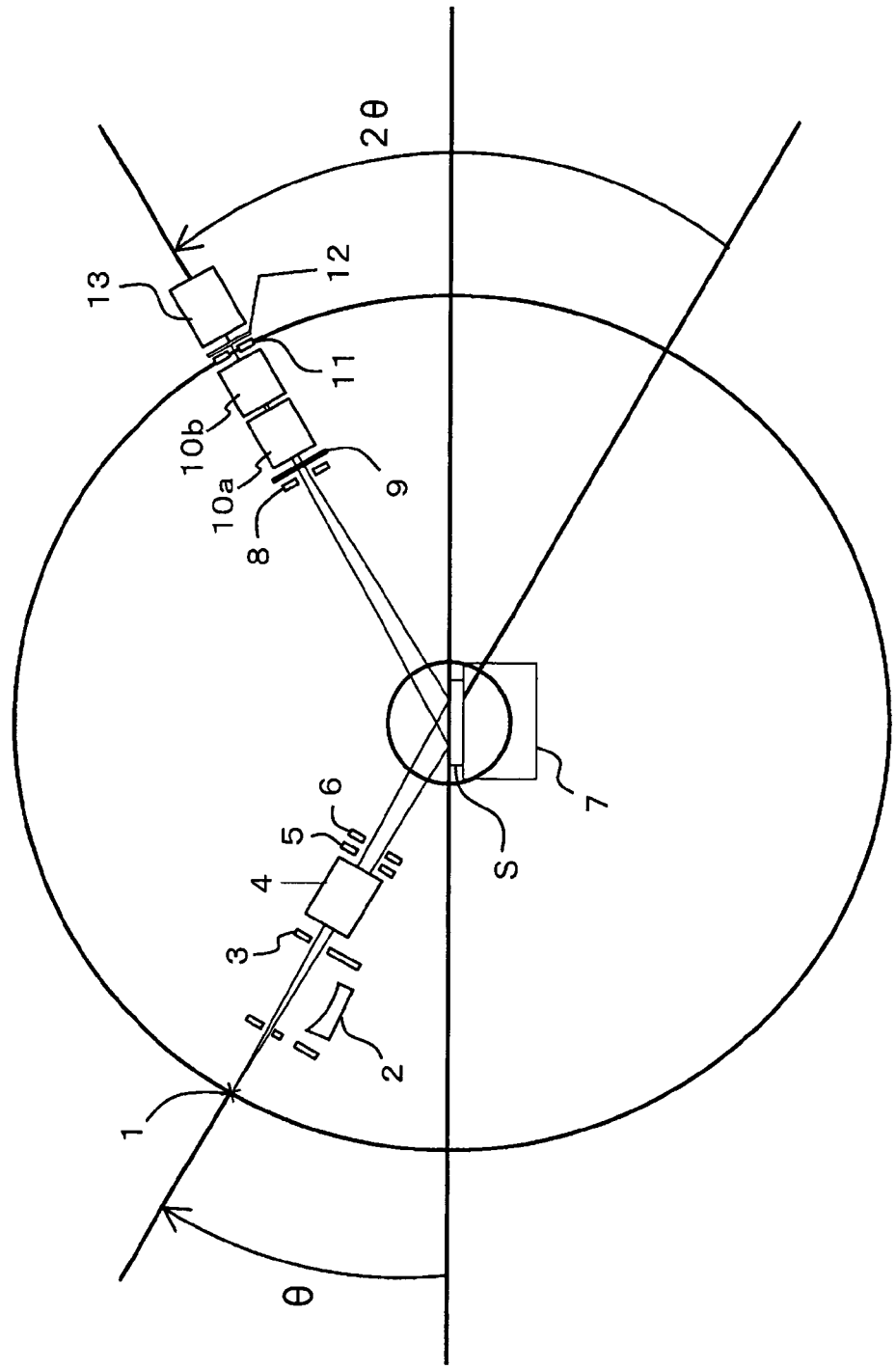
FIG. 27 is a schematic diagram illustrating a constitutional example of a measurement optical system of a conventional X-ray diffraction apparatus.

Also, by appropriately combining the setting of the virtual mask using the virtual mask setting section 26 and the setting of the dimensional mode using the dimensional mode setting section 27, the X-ray diffraction can be measured under various measurement conditions. For instance, as illustrated in FIG. 25, the X-ray diffraction can be measured by setting right and left two opening parts 32-1 and 32-2 in the shield part 33 of the virtual mask 31, and setting the left side opening part 32-1 as one-dimensional mode in the X direction, and setting the right side opening part 32-2 as one-dimensional mode in the Y direction. Also, as illustrated in FIG. 26, the X-ray diffraction can be measured by setting upper and lower two opening parts 32-1 and 32-2 in the shield part 33 of the virtual mask 31, and setting the upper opening part 32-1 as one-dimensional mode in the Y direction, and setting the lower opening part 32-2 as zero-dimensional mode.

8. Effects of Embodiment

In the X-ray diffraction apparatus and the X-ray diffraction method according to an embodiment of the present invention described above, not only the effect described in the following (1), but also the effects described in (2) to (7) can be obtained.

(1) Even if not using the rear optical receiving slit as conventional, the measurement resolution of the X-ray diffraction can be selected by setting the opening dimension of the virtual mask 31 using the virtual mask setting section 26. Therefore, the rear optical receiving slit is not required as an element of the optical receiving system of the X-ray diffraction apparatus. Thus, the cost of the X-ray diffraction apparatus can be reduced.

(2) Since the opening dimension of the virtual mask 31 can be set independently in the X direction and the Y direction using the virtual mask setting section 26, the measurement resolution can be separately determined in the X direction and the Y direction. Therefore, the measurement resolution can be flexibly determined, which is not realized when using the rear optical receiving slit as conventional. Specifically, there is a necessity for simultaneously setting a slit that opens/close in the X direction, and a slit that opens/close in the Y-direction, to select the measurement resolution in the X direction and in the Y direction using a physical slit such as a rear optical receiving slit as conventional. The slit that functions as the rear optical receiving slit should be provided on the gonio-circle. Therefore, when the slit that opens/closes in the Y direction is provided on the gonio-circle, the slit that opens/closes in the X direction cannot be provided on the gonio-circle, due to a positional interference between such two slits. Accordingly, when using the physical slit as conventional, the measurement resolution can be determined only in one direction. Meanwhile, in this embodiment, since the measurement resolution is determined by the virtual mask 31 which does not actually exist, the problem of physical positional interference does not occur. Therefore, even when the measurement resolution desired by the user in the X direction of the virtual mask 31 and the measurement resolution desired by the user in the Y direction of the virtual mask 31 are different, the opening dimension of the virtual mask 31 can be set according to the measurement resolutions desired in the respective directions. Thus, with the measurement resolution can be flexibly determined, which is not realized conventionally.

(3) As the opening condition of the virtual mask that can be set using the virtual mask setting section 26, not only the opening dimension of the virtual mask, but also the setting of the opening center position of the virtual mask can be given. Thus, the opening/closing center position of the virtual mask can be set so as to be shifted from the center position of the detection surface 17 as needed. Therefore, even when the position of the X-rays incident on the detection surface 17 of the detector 15 is shifted before and after installing the monochromator crystals or the like in the optical path of the X-rays, the incident position of the X-rays and the opening/closing center position of the virtual mask can be aligned on the detection surface 17 of the detector 15, by shift of the opening/closing center position of the virtual mask, corresponding to the shift of the position of the X-rays. Accordingly, there is no necessity for providing a moving mechanism for mechanically moving a slit position of the rear optical receiving slit as conventional. Also, while the direction of shifting the opening/closing center position of the rear optical receiving slit by the moving mechanism is conventionally limited to the Y direction, in this embodiment, there is no such limitation, and the opening center position of the virtual mask 31 can be shifted in both X direction and Y direction. Therefore, the opening center position of the virtual mask 31 can be set at a desired position on the detection surface 17 of the detector 15.

(4) As the opening condition of the virtual mask that can be set using the virtual mask setting section 26, not only the opening dimension of the virtual mask, but also the setting of the number of the openings of the virtual mask can be given. Thus, for instance, when the X-ray diffraction is measured by setting the plurality of opening parts 32 having different opening dimensions, the measurement results with different measurement resolutions can be obtained by one measurement.

(5) As the opening condition of the virtual mask that can be set using the virtual mask setting section 26, not only the opening dimension of the virtual mask, but also the opening shape of the virtual mask can be given. Thus, regardless of the shape of the detection surface 17 of the detector 15, the X-ray diffraction can be measured by using a user-preferred opening shape of the virtual mask.

(6) As the opening condition of the virtual mask that can be set using the virtual mask setting section 26, not only the opening dimension of the virtual mask, but also the inclination angle of the opening of the virtual mask can be given. Thus, for instance, when inclination occurs in the sectional shape of the X-rays incident on the detection surface 17 of the detector 15, the inclination angle of the opening of the virtual mask can be set corresponding to the inclination of the sectional shape. Also, when the sample stage 7 or the sample S set thereon is inclined, the inclination angle of the opening of the virtual mask is set corresponding to the inclination of the sample.

(7) The measurement condition setting section 25 includes the dimensional mode setting section 27 in addition to the virtual mask setting section 26. with this structure, the measurement resolution is freely determined in the X direction and in the Y direction, and the dimensional mode of the detector 15 can be set to any one of the zero-dimensional mode, the one-dimensional mode and the two-dimensional mode, by a combination of the virtual mask setting section 26 and the dimensional mode setting section 27. Therefore, for instance, after setting the opening dimension of the virtual mask to a desired size by the virtual mask setting section 26, the detector 15 can function as a zero-dimensional detector, one-dimensional detector or a two-dimensional detector. Also, when for example two openings of the virtual mask are set by the virtual mask setting section 26, the X-ray diffraction can be measured in different dimensional modes, for each opening part 32. Further, in this case, the X-ray diffraction can be measured using different measurement resolutions for each opening part 32. Also, merits of using the detector 15 which is originally the two-dimensional detector in the zero-dimensional mode or the one-dimensional mode are as follows, for instance. Generally, the zero-dimensional mode is utilized when adjusting the optical system of the X-ray diffraction apparatus or adjusting a sample position. Therefore, the X-ray diffraction apparatus must be equipped with zero-dimensional detector when adjusting the sample position or the like. Then, when the X-ray diffraction is measured by the two-dimensional detector thereafter, the detector of the X-ray diffraction apparatus needs to be changed from the zero-dimensional detector to the two-dimensional detector. Meanwhile, when the dimensional mode of the detector 15 can be switched by the dimensional mode setting section 27 as described above, automatic switching can be done, because the X-ray diffraction can be measured in two-dimensional mode without changing (exchanging) the detector after performing position adjustment, etc., of the sample in zero-dimensional mode. Also, since the detector 15 originally has the position resolution, the detector 15 can be used as a virtual slit by using only a fraction of such a position resolution. Further, the measurement of the optical system by the Bragg Brentano pseudo focusing method using the zero-dimensional detector and high-speed measurement using the one-dimensional detector, which are performed in a general X-ray diffraction apparatus, can be performed without changing the arrangement of the optical system. Also, regarding the zero-dimensional detector, even while the cost of the detector itself is lower than the two-dimensional detector, there is a demerit that the high-speed measurement cannot be performed, which can be performed by the two-dimensional detector having the position resolution.

(Reason for not Providing Attenuator)

Here, a reason for not providing an attenuator in the X-ray diffraction apparatus according to an embodiment of the present invention will be described.

Figure 28A:
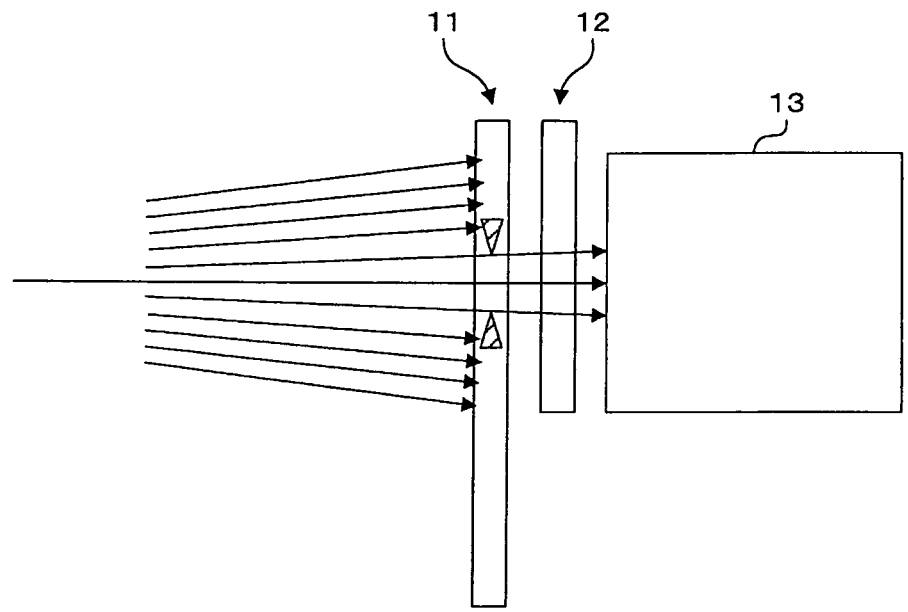
FIGS. 28A and 28B are diagrams for describing relationship between a slit width of a rear optical receiving slit and a measurement resolution.
Figure 28B:
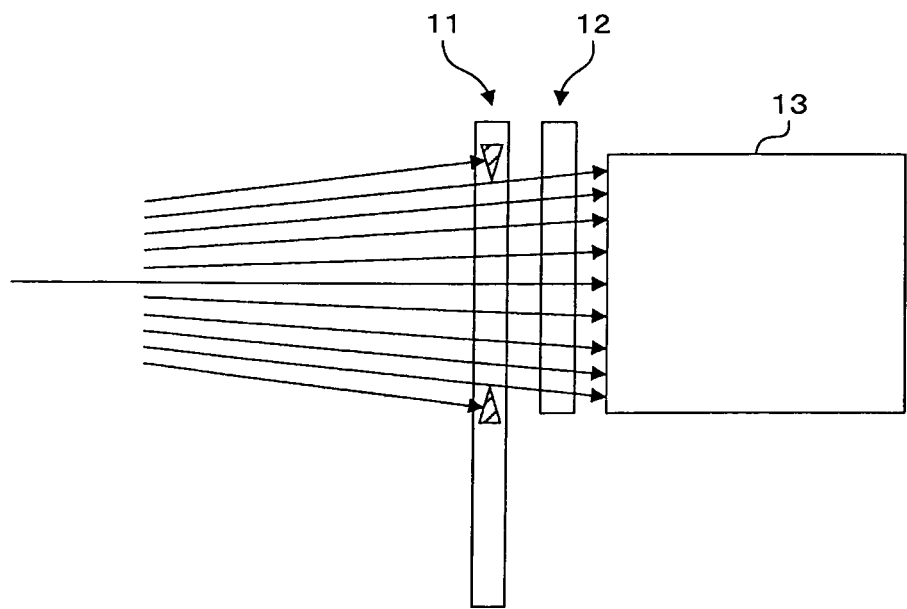

When the intensity of the X-rays incident on the detector 15 is high, conventionally, as illustrated in FIG. 28, by installing an attenuator 12 before the detector 13, the intensity of the X-rays incident on the detector 13 is attenuated by the attenuator 12. Meanwhile, in the embodiment of the present invention, by adopting the detector 15 having a high counting mode, an attenuator-less system is realized. A high counting mode is a counting mode defined as follows: for example, when a counting mode in which the detection signal generated by the detection elements 16 is outputted using two 16 bit circuits in parallel, is defined as a normal counting mode, counting capability (counting limit) of the X-rays is more improved than the normal counting mode. Specifically, in the high counting mode, by using the two 16-bit circuits in series, a counting function practically equal to a 31-bit circuit is realized. Thus, even for the X-rays with high intensity to cause saturation in the normal counting mode, by switching the counting mode applied to the detector 15 from the normal counting mode to the high counting mode, the counting function is improved and the saturation can be prevented. Thus, an expensive attenuator is not required to be installed, and the cost of the X-ray diffraction apparatus can be reduced.

9. Modifications or the Like

The technical scope of the present invention is not limited to the above-described embodiment and includes embodiments variously changed or improved in the range of deriving specific effects that can be obtained by elements of the invention and the combination thereof.

For example, the virtual mask setting step by the virtual mask setting section 26, the X-ray detecting step by the measurement optical system and the signal processing step by the signal processing section 21 may be performed in this order, or may be performed in the following order. Namely, the X-ray detecting step by the measurement optical system is performed first. At this time, the X-ray is detected without setting the virtual mask on the detection surface 17 of the detector 15. Also, all detection signals outputted from the respective detection elements 16 are stored (accumulated) in the memory 22. Next, the virtual mask setting step by the virtual mask setting section 26 is performed, and the Next, the signal processing step by the signal processing section 21 is performed. At this time, the signal processing section 21 reads electric signals from the memory 22 and performs signal processing based on the opening condition of the virtual mask set by the virtual mask setting step. For example, when the opening condition of the virtual mask is set by the condition illustrated in FIG. 7, the electric signals outputted by the detection elements 16 in the opening part 32 of the virtual mask 31 is read from the memory 22 and processing is applied to the signal. When the X-ray diffraction is measured in this order, the electric signals obtained in the X-ray detecting step are temporarily stored once in the memory 22, and therefore if the accumulated detection signals are not deleted, the measurement result based on a desired setting condition can be obtained by changing the setting condition of the virtual mask many times by a user.

Further, the apparatus and the method according to the present invention are widely applicable to various kinds of X-ray diffraction including thin film X-ray diffraction and powder X-ray diffraction or the like, for instance.

What is claimed is:

1. An X-ray diffraction apparatus which irradiates a sample set on a sample stage with X-rays generated from an X-ray source, and detects the X-rays diffracted by the sample using a detector which has a detection surface formed of a plurality of detection elements arrayed two-dimensionally in a first direction and a second direction that are perpendicular to each other, and outputs a detection signal according to intensity of the X-rays received by the detection element, for each of the plurality of detection elements forming the detection surface, the X-ray diffraction apparatus comprising:
    a virtual mask setting section capable of setting a virtual mask on the detection surface of the detector and setting at least an opening dimension of the virtual mask as an opening condition of the virtual mask independently in the first direction and the second direction; and
    a signal processing section which processes the detection signal outputted from the detector according to the opening condition of the virtual mask set by the virtual mask setting section.

2. The X-ray diffraction apparatus according to claim 1, wherein the virtual mask setting section is capable of setting an opening center position of the virtual mask in addition to the opening dimension of the virtual mask, as the opening condition of the virtual mask.

3. The X-ray diffraction apparatus according to claim 1, wherein the virtual mask setting section is capable of setting the number of openings of the virtual mask in addition to the opening dimension of the virtual mask, as the opening condition of the virtual mask.

4. The X-ray diffraction apparatus according to claim 1, wherein the virtual mask setting section is capable of setting an opening shape of the virtual mask in addition to the opening dimension of the virtual mask, as the opening condition of the virtual mask.

5. The X-ray diffraction apparatus according to claim 1, wherein the virtual mask setting section is capable of setting an inclination angle of an opening of the virtual mask in addition to the opening dimension of the virtual mask, as the opening condition of the virtual mask.

6. The X-ray diffraction apparatus according to claim 1, further comprising:
    a dimensional mode setting section which sets a dimensional mode applied when measuring X-ray diffraction using the detector, wherein the signal processing section processes the detection signal outputted from the detector according to the dimensional mode set by the dimensional mode setting section.

7. A method of measuring X-ray diffraction which irradiates a sample set on a sample stage with X-rays generated from an X-ray source, and detects the X-rays diffracted by the sample using a detector which has a detection surface formed of a plurality of detection elements arrayed two-dimensionally in a first direction and a second direction that are perpendicular to each other, and outputs a detection signal according to intensity of the X-rays received by the detection element, for each of the plurality of detection elements forming the detection surface, the method comprising:
    a virtual mask setting step of setting a virtual mask on the detection surface of the detector and setting at least an opening dimension of the virtual mask as an opening condition of the virtual mask independently in the first direction and the second direction;
    an X-ray detecting step of irradiating the sample set on the sample stage with the X-rays generated from the X-ray source, and detecting the X-rays diffracted by the sample using the detector; and
    a signal processing step of processing the detection signal outputted from the detector in the X-ray detecting step, according to the opening condition of the virtual mask set in the virtual mask setting step.

* * * * *